(12) United States Patent
Inubushi et al.

(10) Patent No.: US 9,192,913 B2
(45) Date of Patent: Nov. 24, 2015

(54) ADSORBENT

(75) Inventors: Yasutaka Inubushi, Kurashiki (JP); Takashi Hori, Kurashiki (JP); Toyoaki Kurihara, Chiyoda-ku (JP); Hiroyuki Ogi, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 87 days.

(21) Appl. No.: 14/342,641

(22) PCT Filed: Sep. 4, 2012

(86) PCT No.: PCT/JP2012/072492
§ 371 (c)(1),
(2), (4) Date: Mar. 4, 2014

(87) PCT Pub. No.: WO2013/035702
PCT Pub. Date: Mar. 14, 2013

(65) Prior Publication Data
US 2014/0224120 A1 Aug. 14, 2014

(30) Foreign Application Priority Data
Sep. 5, 2011 (JP) .................................. 2011-192289

(51) Int. Cl.
*B01J 20/22* (2006.01)
*B01D 53/04* (2006.01)
(Continued)

(52) U.S. Cl.
CPC ................. *B01J 20/26* (2013.01); *B01D 53/02* (2013.01); *B01D 53/047* (2013.01);
(Continued)

(58) Field of Classification Search
CPC ............... B01D 53/02; B01D 53/0462; B01D 53/047; B01D 2253/112; B01D 2253/202; B01D 2253/204; B01D 2253/25; B01D 2257/504; B01D 2257/7025; B01D 2259/4525; B01J 20/223; B01J 20/26; B01J 20/261; B01J 20/262; B01J 2220/44; C07C 9/04; C07C 9/06; C07C 7/12; C01B 13/0281; C01B 17/167; C01B 17/60; C01B 21/0455; C01B 21/20; C01B 3/508; C01C 1/006; F17C 11/00; F17C 11/005; F17C 11/007; F17C 1/00; Y02C 10/08; Y02C 20/20
USPC ...................... 95/90, 96, 148, 900, 116, 117, 95/127–130, 136, 138–141, 143; 96/108; 206/0.7; 502/402, 526
See application file for complete search history.

(56) References Cited

U.S. PATENT DOCUMENTS 4,036,944 A * 7/1977 Blytas ........................ 423/658.2
4,081,397 A 3/1978 Booe
(Continued)

FOREIGN PATENT DOCUMENTS

JP  2006 272190  10/2006
JP  2006 297276  11/2006
(Continued)

OTHER PUBLICATIONS

Kajiro, H., et al., "Flexible Two-Dimensional Square-Grid Coordination Polymers: Structures and Functions", Int. J. Mol. Sci., vol. 11, pp. 3803-3845, (2010).
(Continued)

*Primary Examiner* — Frank Lawrence
(74) *Attorney, Agent, or Firm* — Oblon, McClelland, Maier & Neustadt, L.L.P.

(57) ABSTRACT

An object of the present invention is to provide an adsorbent material having excellent gas storage performance and gas separation performance.
This object can be achieved by an adsorbent material comprising a composition comprising a metal complex (A) and an elastomer (B), the metal complex (A) containing an anionic ligand and at least one metal ion selected from ions of metals belonging to Groups 1 to 13 of the periodic table, the metal complex (A) being capable of undergoing a volume change upon adsorption, and the mass ratio of the metal complex (A) and the elastomer (B) being within the range of 1:99 to 99:1.

15 Claims, 9 Drawing Sheets

(51) Int. Cl.

| | |
|---|---|
| *F17C 11/00* | (2006.01) |
| *B01J 20/26* | (2006.01) |
| *B01D 53/02* | (2006.01) |
| *B01D 53/047* | (2006.01) |
| *C07C 7/12* | (2006.01) |
| *F17C 1/00* | (2006.01) |
| *C01B 21/04* | (2006.01) |
| *C01B 21/20* | (2006.01) |
| *C01B 23/00* | (2006.01) |
| *C01B 3/50* | (2006.01) |
| *C01C 1/00* | (2006.01) |
| *C01B 13/02* | (2006.01) |
| *C01B 17/16* | (2006.01) |
| *C01B 17/60* | (2006.01) |

(52) U.S. Cl.
CPC .......... *B01D 53/0462* (2013.01); *B01J 20/223* (2013.01); *B01J 20/261* (2013.01); *B01J 20/262* (2013.01); *C01B 3/508* (2013.01); *C01B 13/0281* (2013.01); *C01B 17/167* (2013.01); *C01B 17/60* (2013.01); *C01B 21/0455* (2013.01); *C01B 21/20* (2013.01); *C01B 23/0057* (2013.01); *C01C 1/006* (2013.01); *C07C 7/12* (2013.01); *F17C 1/00* (2013.01); *B01D 2253/112* (2013.01); *B01D 2253/202* (2013.01); *B01D 2253/204* (2013.01); *B01D 2253/25* (2013.01); *B01D 2257/504* (2013.01); *B01D 2257/7025* (2013.01); *B01D 2259/4525* (2013.01); *B01J 2220/44* (2013.01); *F17C 11/00* (2013.01); *F17C 11/005* (2013.01); *F17C 11/007* (2013.01); *Y02C 10/08* (2013.01); *Y02C 20/20* (2013.01)

(56) References Cited

U.S. PATENT DOCUMENTS

| | | | |
|---|---|---|---|
| 4,134,491 A * | 1/1979 | Turillon et al. | 206/0.7 |
| 4,598,836 A * | 7/1986 | Wessel | 206/0.7 |
| 4,600,525 A * | 7/1986 | Baker et al. | 420/443 |
| 5,662,729 A * | 9/1997 | Nishimura et al. | 75/252 |
| 8,372,184 B2 * | 2/2013 | Zimmermann | 96/108 |
| 2006/0185388 A1 | 8/2006 | Muller et al. | |
| 2007/0227898 A1 | 10/2007 | Muller et al. | |
| 2007/0248852 A1 | 10/2007 | Mueller et al. | |
| 2008/0227634 A1 | 9/2008 | Muller et al. | |
| 2008/0261101 A1 | 10/2008 | De Figueiredo Gomes et al. | |
| 2011/0105776 A1 | 5/2011 | Müller et al. | |
| 2013/0065553 A1 * | 3/2013 | Raleigh | 455/406 |

FOREIGN PATENT DOCUMENTS

| | | |
|---|---|---|
| JP | 2007 533846 | 11/2007 |
| JP | 2008 63413 | 3/2008 |
| JP | 2008-63413 A | 3/2008 |
| JP | 2008 531939 | 8/2008 |
| JP | 2009 517806 | 4/2009 |
| JP | 2009 519116 | 5/2009 |
| JP | 2010 13393 | 1/2010 |
| WO | 03 102000 | 12/2003 |
| WO | WO 2005/049892 A1 | 6/2005 |
| WO | 2006 050898 | 5/2006 |
| WO | 2011 102173 | 8/2011 |
| WO | 2011 105521 | 9/2011 |

OTHER PUBLICATIONS

International Search Report Issued Dec. 4, 2012 in PCT/JP12/072492 Filed Sep. 4, 2012.

Extended European Search Report issued Jul. 8, 2015 in Patent Application No. 12829318.0.

Anja Car et al., "Hybrid Membrane Materials with Different Metal-organic Frameworks (MOFs) for Gas Separation", Desalination, vol. 200, No. 1-3, XP025162232, 2006, pp. 424-426.

* cited by examiner

ADSORBENT

TECHNICAL FIELD

The present invention relates to an adsorbent material. More specifically, the present invention relates to an adsorbent material comprising a composition comprising a metal complex and an elastomer, wherein the metal complex contains an anionic ligand and at least one metal ion selected from ions of metals belonging to Groups 1 to 13 of the periodic table, the metal complex is capable of undergoing a volume change upon adsorption, and the mass ratio of the metal complex and the elastomer is within the range of 1:99 to 99:1. The adsorbent material of the present invention is suitable as an adsorbent material, a storage material, or a separation material for adsorbing, storing, or separating carbon dioxide, hydrogen, carbon monoxide, oxygen, nitrogen, hydrocarbons having 1 to 4 carbon atoms, noble gases, hydrogen sulfide, ammonia, water vapor, organic vapor, and the like.

BACKGROUND ART

In the fields of deodorization, exhaust gas treatment, and the like, various adsorbent materials have so far been developed. Activated carbon is a representative example of these, and it has been used widely in various industries for the purpose of air cleaning, desulfurization, denitrification, or removal of harmful substances by making use of its excellent adsorption performance. In recent years, demand for nitrogen has been increasing, for example, in the semiconductor manufacturing process and the like. Such nitrogen is produced from air by using molecular sieving carbon according to the pressure swing adsorption process or temperature swing adsorption process. Molecular sieving carbon is also used for separation and purification of various gases such as purification of hydrogen from a cracked methanol gas.

When a mixture of gases is separated according to the pressure swing adsorption process or temperature swing adsorption process, it is the common practice to separate it based on the difference between the gases in equilibrium adsorption amount or rate of adsorption to molecular sieving carbon or zeolite used as a separation adsorbent material. When the mixture of gases is separated based on the difference in equilibrium adsorption amount, conventional adsorbent materials cannot selectively adsorb thereto only the gas to be removed, and the separation coefficient decreases, making it inevitable that the size of the apparatus used therefor increases. When the mixture of gases is separated into individual gases based on the difference in rate of adsorption, on the other hand, only the gas to be removed can be adsorbed, although it depends on the kind of gas. It is necessary, however, to alternately carry out adsorption and desorption, and also in this case, the apparatus used therefor should be larger.

On the other hand, there has also been developed, as an adsorbent material providing superior adsorption performance, a coordination polymer undergoing a change in dynamic structure when exposed to external stimulation. When this novel coordination polymer undergoing a change in dynamic structure is used as a gas adsorbent material, it does not adsorb a gas until a predetermined pressure but it starts gas adsorption at a pressure exceeding the predetermined pressure. In addition, a phenomenon is observed in which the adsorption starting pressure differs depending on the nature of the gas.

Application of these phenomena to adsorbent materials used in a gas separation apparatus employing a pressure swing adsorption system enables very efficient gas separation. It can also decrease the pressure swing width, contributing to energy savings. Further, it can contribute to size reduction of the gas separation apparatus, making it possible to increase competitiveness in terms of costs when a high-purity gas is put on the market as a product. Moreover, even if the high-purity gas is used in a company's own plant, the costs paid for the equipment requiring a high-purity gas can be reduced, resulting in a reduction of manufacturing costs of the final product.

When a coordination polymer is used as an adsorbent material, it is preferable to use the coordination polymer after molding, rather than in the form of a powder. For example, pelletization by tablet compression is known as a method of molding a coordination polymer (see PTL 1 and PTL 2). However, when the present inventors pelletized, by tablet compression, a coordination polymer undergoing a change in dynamic structure when exposed to external stimulation, it was confirmed that the pellet form could not be maintained after adsorption of gas, because the volume of the coordination polymer undergoing a change in dynamic structure when exposed to external stimulation was expanded upon gas adsorption (see, for example, NPL 1).

Regarding a coordination polymer comprising a copper ion, a tetrafluoroborate ion, and 4,4'-bipyridyl, it is known that the coordination polymer can be formed into pellets by tablet compression when using magnesium stearate as a lubricant, and that the coordination polymer can be formed into granules by using sugar as a binder (see NPL 1). However, the methane adsorption starting pressure of pelletized samples becomes about 1 MPa higher than the starting pressure of powder samples. Thus, the original properties of the coordination polymer cannot be maintained after pelletization.

PTL 3 discloses a heat-conductive resin composition comprising a porous coordination polymer and a thermoplastic resin. As specific examples of the thermoplastic resin, PTL 3 refers to styrene elastomers, polyester elastomers, polyurethane elastomers, and olefin elastomers; however, the obtained composition is not designed for gas adsorption, and nothing of this sort is mentioned in PTL 3.

CITATION LIST

Patent Literature

PTL 1: WO2003/102000
PTL 2: WO2006/050898
PTL 3: JP2008-63413A

Non-Patent Literature

NPL 1: H. Kajiro, A. Kondo, K. Kaneko, and H. Kanoh, International Journal of Molecular Sciences, vol. 11, pp. 3803-3845 (2010)

SUMMARY OF INVENTION

Technical Problem

Accordingly, a primary object of the present invention is to provide an adsorbent material that can be used as a gas adsorption material having a higher adsorption amount than conventional materials, a gas storage material having a high effective storage amount, or a gas separation material having higher selectivity than conventional materials. A second object of the present invention is to provide an adsorbent material obtained by molding a composition comprising a coordination polymer as a component, the adsorbent material maintaining its shape after adsorption of gas, etc., and exhibiting gas adsorption/desorption ability equal to that of the composition before molding.

Solution to Problem

As a result of intensive study, the present inventors found that the above objects can be achieved by a composition comprising a metal complex (A) and an elastomer (B), the metal complex (A) containing an anionic ligand and at least one metal ion selected from ions of metals belonging to Groups 1 to 13 of the periodic table, the metal complex (A) being capable of undergoing a volume change upon adsorption, and the mass ratio of the metal complex (A) and the elastomer (B) being within the range of 1:99 to 99:1. Thus, the present invention has been completed.

Specifically, the present invention provides the following.
(1) An adsorbent material comprising a composition comprising a metal complex (A) and an elastomer (B),
 the metal complex (A) containing an anionic ligand and at least one metal ion selected from ions of metals belonging to Groups 1 to 13 of the periodic table,
 the metal complex (A) being capable of undergoing a volume change upon adsorption, and
 the mass ratio of the metal complex (A) and the elastomer (B) being within the range of 1:99 to 99:1.
(2) The adsorbent material according to (1), wherein the metal complex (A) contains an organic ligand capable of multidentate binding to the metal ion.
3) The adsorbent material according to (1) or (2), wherein the volume change rate of the metal complex (A) upon adsorption is 0.5 to 50%.
(4) The adsorbent material according to any one of (1) to (3), wherein the elastomer (B) is a thermoplastic elastomer that has at least one polymer block having a glass transition temperature of 273 K or less.
(5) The adsorbent material according to any one of (1) to (4), wherein the adsorbent material is for adsorbing carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.
(6) A storage material comprising the adsorbent material of any one of (1) to (4).
(7) The storage material according to (6), wherein the storage material is for storing carbon dioxide, hydrogen, carbon monoxide, oxygen, nitrogen, hydrocarbons having 1 to 4 carbon atoms, noble gases, hydrogen sulfide, ammonia, water vapor, or organic vapor.
(8) A gas storage device comprising a pressure-resistant container that can be hermetically sealed and that has an inlet and outlet for gas,
 the pressure-resistant container having a gas storage space therein, and
 the storage material of (6) being placed in the gas storage space.
(9) A gaseous-fuel vehicle comprising an internal combustion engine that obtains driving force from fuel gas supplied from the gas storage device of (8).
(10) A separation material comprising the adsorbent material of any one of (1) to (4).
(11) The separation material according to (10), wherein the separation material is for separating carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.
(12) A separation method using the separation material of (10), the method comprising the step of bringing the separation material and a gas mixture into contact with each other in a pressure range of 0.01 to 10 MPa.
(13) The separation method according to (12), wherein the separation method is a pressure swing adsorption process or a temperature swing adsorption process.

Advantageous Effects of Invention

The present invention provides an adsorbent material comprising a composition comprising a metal complex (A) and an elastomer (B), the metal complex (A) containing an anionic ligand and at least one metal ion selected from ions of metals belonging to Groups 1 to 13 of the periodic table, the metal complex (A) being capable of undergoing a volume change upon adsorption, and the mass ratio of the metal complex (A) and the elastomer (B) being within the range of 1:99 to 99:1.

Due to its superior adsorption performance with respect to various gases, the adsorbent material of the present invention can be used as an adsorbent material for adsorbing carbon dioxide, hydrogen, carbon monoxide, oxygen, nitrogen, hydrocarbons having 1 to 4 carbon atoms, noble gases, hydrogen sulfide, ammonia, water vapor, organic vapor, and the like.

Further, due to its superior storage performance with respect to various gases, the storage material of the present invention can also be used as a storage material for storing carbon dioxide, hydrogen, carbon monoxide, oxygen, nitrogen, hydrocarbons having 1 to 4 carbon atoms, noble gases, hydrogen sulfide, ammonia, water vapor, organic vapor, and the like.

Furthermore, due to its superior separation performance with respect to various gases, the separation material of the present invention can further be used as a separation material for separating carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, organic vapor, and the like.

The adsorbent material of the present invention undergoes almost no volume expansion after molding, along with the volume change of the coordination polymer when it adsorbs gas, etc. The shape of the adsorbent material is maintained even after adsorption. Moreover, the adsorbent material of the present invention maintains the gas adsorption/desorption ability inherent in the coordination polymer even after molding, and exhibits adsorption performance, storage performance, and separation performance that are equal to those before molding.

DESCRIPTION OF EMBODIMENTS

Figure 1:
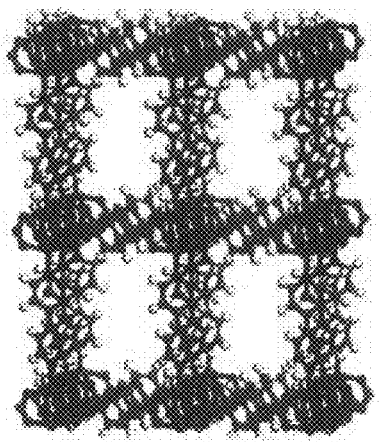
FIG. 1: A schematic diagram illustrating a jungle-gym-type framework in which 4,4'-bipyridyl is coordinated to the axial position of a metal ion in a paddle-wheel-type framework composed of a metal ion and a carboxylate ion of terephthalic acid.

The adsorbent material of the present invention comprises a composition comprising a metal complex (A) and an elastomer (B), wherein the metal complex (A) contains an anionic ligand and at least one metal ion selected from ions of metals belonging to Groups 1 to 13 of the periodic table, the metal complex (A) is capable of undergoing a volume change upon adsorption, and the mass ratio of the metal complex (A) and the elastomer (B) is 1:99 to 99:1.

The metal ion contained in the metal complex (A) is at least one member selected from ions of metals belonging to Groups 1 to 13 of the periodic table. Ions of metals belonging to Group 1 of the periodic table include lithium, sodium, potassium, rubidium, cesium, and francium ions. Ions of metals belonging to Group 2 of the periodic table include beryllium, magnesium, calcium, strontium, barium, and radium ions. Ions of metals belonging to Group 3 of the periodic table include scandium, yttrium, lanthanoid, and actinoid ions. Ions of metals belonging to Group 4 of the periodic table include titanium, zirconium, hafnium, and rutherfordium ions. Ions of metals belonging to Group 5 of the periodic table include vanadium, niobium, tantalum, and dubnium ions. Ions of metals belonging to Group 6 of the periodic table include chromium, molybdenum, tungsten, and seaborgium ions. Ions of metals belonging to Group 7 of the periodic table include manganese, technetium, rhenium, and bohrium ions. Ions of metals belonging to Group 8 of the periodic table include iron, ruthenium, osmium, and hassium ions. Ions of metals belonging to Group 9 of the periodic table include cobalt, rhodium, iridium, and meitnerium ions. Ions of metals belonging to Group 10 of the periodic table include nickel, palladium, platinum, and darmstadtium ions. Ions of metals belonging to Group 11 of the periodic table include copper, silver, gold, and roentgenium ions. Ions of metals belonging to Group 12 of the periodic table include zinc, cadmium, mercury, and ununbium ions. Ions of metals belonging to Group 13 of the periodic table include boron, aluminium, gallium, indium, thallium, and ununtrium ions.

Examples of the metal ion used in the metal complex (A) and selected from ions of metals belonging to Group 1 to 13 of the periodic table include lithium, potassium, magnesium, calcium, barium, scandium, zirconium, vanadium, chromium, manganese, iron, ruthenium, cobalt, rhodium, nickel, palladium, copper, zinc, cadmium, and aluminum ions. It is preferable to use a single metal ion; however, it is also possible to use a metal complex mixture containing two or more metal ions. The metal complex (A) used in the present invention may be a mixture of two or more metal complexes each containing a single metal ion.

Metal salts containing metal ions mentioned above can be used in the production of the metal complex (A). Examples of metal salts include lithium salts, potassium salts, magnesium salts, calcium salts, barium salts, scandium salts, zirconium salts, vanadium salts, chromium salts, manganese salts, iron salts, ruthenium salts, cobalt salts, rhodium salts, nickel salts, palladium salts, copper salts, zinc salts, cadmium salts, aluminum salts, and the like. It is preferable to use a single metal salt; however, it is also possible to mix two or more metal salts. Examples of such metal salts include organic acid salts such as acetates or formates, and inorganic acid salts such as sulfates, nitrates, carbonates, hydrochlorides, or hydrobromates.

Examples of the anionic ligand used in the metal complex (A) include halide ions, such as fluoride, chloride, bromide, and iodide ions; inorganic acid ions, such as tetrafluoroborate, hexafluorosilicate, hexafluorophosphate, hexafluoroarsenate, and hexafluoroantimonate ions; sulfonate ions, such as trifluoromethanesulfonate and benzenesulfonate ions; aliphatic monocarboxylate ions, such as formate, acetate, trifluoroacetate, propionate, butyrate, isobutyrate, valerate, caproate, enanthate, cyclohexanecarboxylate, caprylate, octylate, pelargonate, caprate, laurate, myristate, pentadecylate, palmitate, margarate, stearate, tuberculostearate, arachidate, behenate, lignocerate, α-linolenate, eicosapentaenoate, docosahexaenoate, linoleate, and oleate ions; aromatic monocarboxylate ions, such as benzoate, 2,5-dihydroxybenzoate, 3,7-dihydroxy-2-naphthoate, 2,6-dihydroxy-1-naphthoate, and 4,4'-dihydroxybiphenyl-3-carboxylate ions; heteroaromatic monocarboxylate ions, such as nicotinate and isonicotinate ions; aliphatic dicarboxylic acid ions, such as 1,4-cyclohexanedicarboxylate and fumarate ions; aromatic dicarboxylate ions, such as 1,3-benzenedicarboxylate, 1,4-benzenedicarboxylate, 1,4-naphthalenedicarboxylate, 2,6-naphthalenedicarboxylate, 2,7-naphthalenedicarboxylate, and 4,4'-biphenyldicarboxylate ions; heteroaromatic dicarboxylate ions, such as 2,5-thiophenedicarboxylate, 2,2'-dithiophenedicarboxylate, 2,3-pyrazinedicarboxylate, 2,5-pyridinedicarboxylate, and 3,5-pyridinedicarboxylate ions; aromatic tricarboxylate ions, such as 1,3,5-benzenetricarboxylate and 1,3,4-benzenetricarboxylate ions; aromatic tetracarboxylate ions, such as 1,2,4,5-benzenetetracarboxylate ions; ions of heterocyclic compounds, such as imidazolate, 2-methylimidazolate, and benzoimidazolate ions; and the like. Here, "anionic ligand" refers to a ligand in which the coordination site for the metal ion is anionic.

Preferable anionic ligands among the above examples are those having a carboxylate group. More specifically, the anionic ligand is preferably selected from aliphatic monocarboxylate ions, aromatic monocarboxylate ions, heteroaromatic monocarboxylate ions, aliphatic dicarboxylate ions, aromatic dicarboxylate ions, heteroaromatic dicarboxylate ions, aromatic tricarboxylate ions, and aromatic tetracarboxylate ions.

When the anionic ligand is an organic ligand having a carboxylate group, a sulfonate group, or the like, the organic ligand may further have a non-ionizable substituent, in addition to a substituent that can become an anion, such as a carboxyl group or a sulfo group. For example, the 1,4-benzenedicarboxylate ion may be a 2-nitro-1,4-benzenedicarboxylate ion. The number of substituents is preferably 1, 2, or 3. Examples of substituents include, but are not limited to, alkyl groups (linear or branched alkyl groups having 1 to 5 carbon atoms, such as methyl, ethyl, n-propyl, isopropyl, n-butyl, isobutyl, tert-butyl, and pentyl), halogen atoms (fluorine, chlorine, bromine, and iodine), alkoxy groups (e.g., methoxy, ethoxy, n-propoxy, isopropoxy, n-butoxy, isobutoxy, and tert-butoxy), amino groups, monoalkylamino groups (e.g., methylamino), dialkylamino groups (e.g., dimethylamino), formyl groups, epoxy groups, acyloxy groups (e.g., acetoxy, n-propanoyloxy, n-butanoyloxy, pivaloyloxy, and benzoyloxy), alkoxycarbonyl groups (e.g., methoxycarbonyl, ethoxycarbonyl, and n-butoxycarbonyl), nitro groups, cyano groups, hydroxyl groups, acetyl groups, trifluoromethyl groups, and the like.

The anionic ligand used in the metal complex (A) may be only a single anionic ligand or a combination of two or more anionic ligands. The metal complex (A) may be a mixture of two or more metal complexes each containing a single anionic ligand.

A salt containing an anionic ligand mentioned above can be used in the production of the metal complex (A). Usable examples of salts include lithium salts, sodium salts, potassium salts, ammonium salts, and the like. It is preferable to use a single salt; however, it is also possible to use a mixture of two or more salts.

The anionic ligand used in the metal complex (A) may be a counteranion of the metal salt used as the metal ion source.

Further, a conjugate acid containing an anionic ligand mentioned above or acid anhydride thereof can be used in the production of the metal complex (A). It is preferable to use a single acid; however, it is also possible to use a mixture of two or more acids.

The metal complex (A) used in the present invention is capable of adsorbing a substance and undergoing a volume change upon adsorption. The volume change of the metal complex in the present specification is defined as the change of volume resulting from changes in the structure and size of pores in the complex framework that occur when a substance is adsorbed to the pores of the metal complex. Examples of the substance to be adsorbed to the pores include gaseous substances, such as carbon dioxide, hydrogen, carbon monoxide, oxygen, nitrogen, hydrocarbons having 1 to 4 carbon atoms, noble gases, and ammonia; and liquid substances, such as water and organic compounds that are in liquid form at ordinary temperature under ordinary pressure.

The volume change rate of the metal complex (A) used in the present invention upon adsorption is preferably 0.5% to 50%. The volume change rate as mentioned herein is defined as the volume ratio of the structural unit of the metal complex (A) before and after adsorption. The volume of the structural unit of the metal complex (A) can be determined by, but is not limited to, single-crystal X-ray structure analysis or powder X-ray crystal structure analysis.

For example, the volume change rate can be determined by using, as a reference volume, the volume of the metal complex left at ordinary temperature under ordinary pressure after vacuum drying, and comparing the reference volume with the volume of the metal complex increased from the reference volume when the metal complex is immersed in a solvent used in the complex forming reaction. Specific examples of the solvent include methanol, ethanol, propanol, diethyl ether, dimethoxyethane, tetrahydrofuran, hexane, cyclohexane, heptane, benzene, toluene, methylene chloride, chloroform, acetone, ethyl acetate, acetonitrile, N,N-dimethylformamide, water, and mixed solvents thereof. The immersion temperature is preferably 253 to 423 K.

The metal complex (A) used in the present invention may contain an organic ligand capable of multidentate binding to the metal ions mentioned above. Examples of organic ligands capable of multidentate binding include bidentate organic ligands, such as 1,4-diazabicyclo[2.2.2]octane, pyrazine, 2,5-dimethylpyrazine, 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 4,4'-dipyridylsulfide, 1,3-bis(4-pyridyl)propane, 1,2-bis(4-pyridyl)-glycol, N-(4-pyridyl)isonicotinamide, and 4,4'-bipyridine-N,N'-dioxide; tridentate organic ligands, such as 2,4,6-tri(4-pyridyl)-1,3,5-triazine; and tetradentate organic ligands, such as tetrakis(3-pyridyloxymethylene)methane and tetrakis(4-pyridyloxymethylene)methane. Here, "neutral organic ligand capable of multidentate binding" refers to a neutral ligand having at least two sites coordinated to a metal ion with a lone electron pair. "Bidentate organic ligand" refers to a neutral organic ligand capable of multidentate binding and having two sites coordinated to a metal ion with a lone electron pair. "Tridentate organic ligand" refers to a neutral organic ligand capable of multidentate binding and having three sites coordinated to a metal ion with a lone electron pair. "Tetradentate organic ligand" refers to a neutral organic ligand capable of multidentate binding and having four sites coordinated to a metal ion with a lone electron pair.

The organic ligand capable of multidentate binding may have a substituent. Examples of substituents include, but are not limited to, alkyl groups (linear or branched alkyl groups having 1 to 5 carbon atoms, such as methyl, ethyl, n-propyl, isopropyl, n-butyl, isobutyl, tert-butyl, and pentyl), halogen atoms (fluorine, chlorine, bromine, and iodine), alkoxy groups (e.g., methoxy, ethoxy, n-propoxy, isopropoxy, n-butoxy, isobutoxy, and tert-butoxy), amino groups, monoalkylamino groups (e.g., methylamino), dialkylamino groups (e.g., dimethylamino), formyl groups, epoxy groups, acyloxy groups (e.g., acetoxy, n-propanoyloxy, n-butanoyloxy, pivaloyloxy, and benzoyloxy), alkoxycarbonyl groups (e.g., methoxycarbonyl, ethoxycarbonyl, and n-butoxycarbonyl), nitro groups, cyano groups, hydroxyl groups, acetyl groups, trifluoromethyl groups, and the like.

The metal complex (A) may contain only one organic ligand capable of multidentate binding, or two or more organic ligands capable of multidentate binding. The metal complex (A) may be a mixture of two or more metal complexes containing a single organic ligand capable of multidentate binding.

The metal complex (A) may further contain a monodentate organic ligand, as long as the effect of the present invention is not impaired. "Monodentate organic ligand" refers to a neutral ligand having one site coordinated to a metal ion with a lone electron pair. Examples of monodentate organic ligands include furan, thiophene, pyridine, quinoline, isoquinoline, acridine, triphenyl phosphine, triphenyl phosphite, methylisocyanide, and the like. Of these, pyridine is preferable. The monodentate organic ligand may be substituted with a hydrocarbon group having 1 to 23 carbon atoms.

When the metal complex (A) contains such a monodentate organic ligand, the composition ratio of the organic ligand capable of multidentate binding to the monodentate organic ligand is preferably in the following molar ratio: organic ligand capable of multidentate binding:monodentate organic ligand=1:5 to 1:1,000, more preferably 1:10 to 1:100, although the ratio is not limited as long as the effect of the present invention is not impaired. The composition ratio can be determined by analysis using, for example, gas chromatography, high-performance liquid chromatography, or NMR; however, the method is not limited to these.

The metal complex (A) used in the present invention can be produced by reacting a metal salt containing at least one metal ion selected from ions of metals belonging to Groups 1 to 13 of the periodic table, a compound containing an anionic ligand, and optionally an organic ligand capable of multidentate binding to the metal ion, in vapor phase, liquid phase, or solid phase. In particular, it is preferable to produce the metal complex (A) by reacting these components in a solvent under ordinary pressure for several hours to several days, and precipitating them. For example, the metal complex (A) used in the present invention can be obtained by mixing and reacting an aqueous solution or organic solvent solution of a metal salt with an organic solvent solution containing an anionic ligand and an organic ligand capable of multidentate binding, under ordinary pressure.

The mixing ratio of the metal salt to the anionic ligand during the production of the metal complex (A) preferably falls in the following molar ratio: metal salt:anionic ligand=1:10 to 10:1, more preferably 1:5 to 5:1. If the mixing ratio falls out of this range during the reaction, the yield decreases and side reaction increases, even though the target metal complex can be obtained.

The molar concentration of the anionic ligand in the mixed solution used for the production of the metal complex (A) is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range, the solubility decreases, thereby hindering the progress of reaction.

The molar concentration of the metal salt in the mixed solution used for the production of the metal complex (A) is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range, residues of unreacted metal salts are generated, thereby causing complication in the purification process of the resulting metal complex.

When the metal complex (A) contains an organic ligand capable of multidentate binding, the mixing ratio of the anionic ligand to the organic ligand capable of multidentate binding during the production of the metal complex (A) is preferably in the following molar ratio: anionic ligand:organic ligand capable of multidentate binding=1:5 to 8:1, more preferably 1:3 to 6:1. The mixing ratio of the metal salt to the organic ligand capable of multidentate binding preferably falls in the following molar ratio: metal salt:organic ligand capable of multidentate binding=3:1 to 1:3, more preferably 2:1 to 1:2.

The solvent used for the production of a metal complex may be an organic solvent, water, or a mixed solvent of these. Specific examples of the solvent include methanol, ethanol, propanol, diethyl ether, dimethoxyethane, tetrahydrofuran, hexane, cyclohexane, heptane, benzene, toluene, methylene chloride, chloroform, acetone, ethyl acetate, acetonitrile, N,N-dimethylformamide, water, and mixed solvents of these. The reaction temperature is preferably 253 to 423 K.

The completion of the reaction may be confirmed by, for example, analyzing the remaining amount of the raw materials by using gas chromatography or high-performance liquid chromatography; however, the method is not limited to these. After the reaction is completed, the resulting mixture is subjected to suction filtration to collect the precipitates. The precipitates are washed with an organic solvent and dried under vacuum for several hours at about 373 K, thereby yielding the metal complex (A) to be used in the present invention.

The metal complex (A) used in the present invention cannot adsorb gases when it adsorbs a solvent. Accordingly, when the metal complex (A) is used as the adsorbent material of the present invention, it is necessary to previously dry the metal complex (A) under vacuum to remove the solvent in the pores. The vacuum drying may be generally performed at a temperature that does not decompose the metal complex (A) (e.g., 298 K to 523 K or less); however, an even lower temperature (e.g., 298 K to 393 K or less) is preferable. This operation may be replaced by washing with supercritical carbon dioxide.

The metal complex (A) used in the present invention is a metal complex that has a one-dimensional, two-dimensional, or three-dimensional framework, depending on the type of anionic ligand used, and the type of organic ligand capable of multidentate binding, when used, and that is capable of undergoing a volume change upon adsorption.

Figure 2:
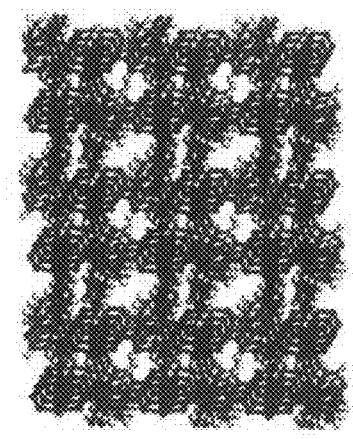
FIG. 2: A schematic diagram illustrating a three-dimensional structure in which two jungle-gym-type frameworks are interpenetrated into each other.

As an example of the metal complex capable of undergoing a volume change upon adsorption, the following describes, in detail, a metal complex (A-1) having a zinc ion as a metal ion, 1,4-benzenedicarboxylate (terephthalate ion) as an anionic ligand, and 4,4'-bipyridyl as an organic ligand capable of multidentate binding. The metal complex (A-1) has a three-dimensional structure in which two jungle-gym-type frameworks are interpenetrated into each other. The jungle-gym-type framework is structured such that 4,4'-bipyridyl is coordinated to the axial position of a metal ion in a paddle-wheel-type framework composed of a metal ion and a carboxylate ion of 1,4-benzenedicarboxylate. FIG. 1 is a schematic diagram illustrating a jungle-gym-type framework, and FIG. 2 is a schematic diagram illustrating a three-dimensional structure in which two jungle-gym-type frameworks are interpenetrated into each other.

"Jungle-gym-type framework" refers to a jungle-gym-like three-dimensional structure in which an organic ligand capable of multidentate binding, such as 4,4'-bipyridyl, is coordinated to the axial position of a metal ion in a paddle-wheel-type framework composed of a metal ion and an anionic ligand, such as 1,4-benzenedicarboxylate, thus connecting the two-dimensional lattice sheets composed of the anionic ligand and the metal ion. "Structure in which multiple jungle-gym-type frameworks are interpenetrated into each other" indicates a three-dimensional framework in which multiple jungle-gym-type frameworks are interpenetrated to each other by filling each other's pores.

"Metal complex capable of undergoing a volume change upon adsorption" in the present specification refers to a metal complex that undergoes changes in the structure and size of pores in the framework due to chemical stimulation caused by the adsorption of a substance into the pores of the metal complex. The metal complex may undergo a volume change upon not only chemical stimulation, but also physical stimulation, such as temperature, pressure, and electric field.

Figure 3:
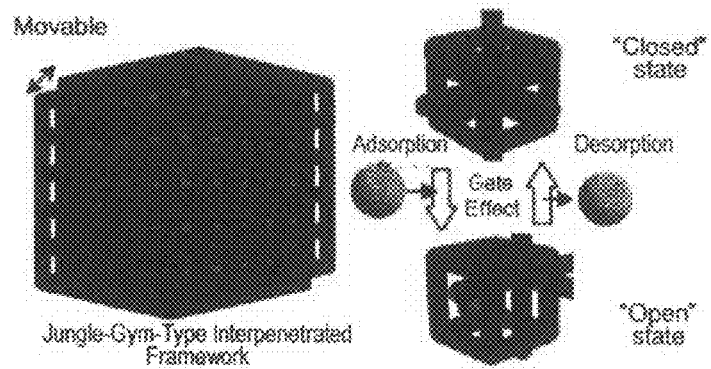
FIG. 3: A schematic diagram illustrating structural change of the metal complex of the present invention upon adsorption and desorption.

The changes in the structure and size of the pores of the metal complex depend on the type of substance to be adsorbed, adsorption pressure, and adsorption temperature. This means that the degree of the structural change differs with the substance to be adsorbed as well as the difference in the interaction between the pore surface and the substance (the intensity of the interaction being in proportion to the magnitude of the Lennard-Jones potential of the substance). FIG. 3 shows a schematic diagram illustrating an example of structural change upon adsorption and desorption when the metal complex (A) has a jungle-gym-type framework.

Other examples of the metal complex capable of undergoing a volume change upon adsorption include a metal complex having a three-dimensional structure composed of integrated one-dimensional frameworks obtained by using a copper ion as a metal ion, a tetrafluoroborate ion as an anionic ligand, and 1,2-bis(4-pyridyl)ethane as an organic ligand capable of multidentate binding; a metal complex having a three-dimensional structure composed of laminated two-dimensional lattice frameworks obtained by using a copper ion as a metal ion, a tetrafluoroborate ion as an anionic ligand, and 4,4'-bipyridyl as an organic ligand capable of multidentate binding; a metal complex having a three-dimensional structure composed of interdigitated two-dimensional-sheet-type frameworks obtained by using a copper ion as a metal ion, a 2,5-dihydroxybenzoate ion as an anionic ligand, and 4,4'-bipyridyl as an organic ligand capable of multidentate binding; and the like.

The three-dimensional integrated structure of the metal complex (A) can be confirmed by, for example, single-crystal X-ray structure analysis or powder X-ray crystal structure analysis; however, the method is not limited to these.

The capability of the metal complex (A) used in the present invention to undergo a volume change upon adsorption can be confirmed by, for example, comparison of the results of single-crystal X-ray structure analysis, changes in powder X-ray diffraction patterns, changes in absorption wavelength, or changes in magnetic susceptibility.

The elastomer (B) used in the present invention is not limited, and any elastomer can be used. In particular, thermoplastic elastomers are preferable. Usable thermoplastic elastomers are block copolymers having, as part of the polymer chain, at least one polymer block (rubber phase) with a glass transition temperature of 273 K or less (e.g., a glass transition temperature of 173 K or more and 273 K or less). Particularly preferable thermoplastic elastomers are block copolymers having, as part of the polymer chain, a polymer block (rubber phase) with a glass transition temperature of 273 K or less, and a polymer block (constrained phase) with a glass transition temperature of 310 K or more (e.g., a glass transition temperature of 310 K or more and 393 K or less).

Examples of the thermoplastic elastomer used in the present invention include styrene elastomers, olefin elastomers, urethane elastomers, polyester elastomers, nitrile elastomers, amide elastomers, polybutadiene elastomers, acrylic elastomers, and vinyl chloride thermoplastic elastomers. Of these, styrene elastomers, olefin elastomers, and acrylic elastomers are particularly preferably used.

The mixing ratio of the metal complex (A) to the elastomer (B) is preferably in the following molar ratio: metal complex (A):elastomer (B)=1:99 to 99:1, more preferably 10:90 to 90:10. If the mixing ratio falls out of this range, gas adsorption performance may be degraded, and/or the form as a composition may not be maintained.

The method of mixing the metal complex (A) and the elastomer (B) is not limited. Specifically, a melt-kneading method is preferred in terms of simple processes and costs. In this case, it is preferable to use an apparatus that can achieve a high degree of kneading, so as to disperse each component finely and uniformly, in terms of enhancing gas adsorption performance, gas storage performance, and gas separation performance, as well as preventing formation and contamination of gels and hard spots.

Examples of the apparatus that can achieve a high degree of kneading include, but are not limited to, continuous-type kneaders, such as a continuous-type intensive mixer, a kneading-type twin-screw extruder, a mixing roll, and a co-kneader; batch-type kneaders, such as a high-speed mixer, a Banbury mixer, an intensive mixer, and a pressurizing kneader; devices using a rotating disk with a mill mechanism, such as a stone mill; single-screw extruders equipped with a kneading section (e.g., Dulmage and CTM); simple kneaders, such as a ribbon blender and a Brabender mixer; and the like.

The kneading temperature is generally within the range of 300 to 600 K. In order to prevent oxidation deterioration of the metal complex (A) and the elastomer (B), it is preferable to seal the opening of the hopper with nitrogen and perform extrusion at a low temperature. The kneading time is generally 10 to 1,800 seconds, preferably 15 to 1,000 seconds, in view of preventing oxidation deterioration of the metal complex (A) and the elastomer (B), and in terms of production efficiency.

The form of the composition used in the present invention is not limited, and any molded body is can be used as long as it is produced by using the composition comprising the metal complex (A) and the elastomer (B). Examples of the form of the composition include pellets, films, sheets, plates, pipes, tubes, rods, granules, powders, various special molded products, fibers, hollow filaments, woven fabrics, knitted fabrics, non-woven fabrics, and the like.

When the composition of the present invention is used as a pellet, the diameter of the pellet preferably falls in a range of 1.5 mm to 5.0 mm, and the length preferably falls in a range of 1.0 mm to 5.0 mm.

When the composition of the present invention is used as a separation film, the composition is preferably in the form of a film or a hollow filament in terms of the permeability of gas molecules, selectivity, and treatment efficiency; and more preferably a hollow filament in terms of treatment efficiency.

The film can be formed by, for example, dispersing or dissolving the metal complex (A) and the elastomer (B) used in the present invention in a suitable solvent to prepare a liquid composition, and applying the liquid composition to a removable base or substrate, followed by drying to remove the solvent. Examples of the solvent for dispersing or dissolving the metal complex (A) and the elastomer (B) include, but are not limited to, toluene, tetrahydrofuran, and the like.

The method for applying the composition used in the present invention to a removable base or substrate is not limited, and any coating method using a known liquid coating material can be used. Examples include immersion coating, spray coating, spinner coating, bead coating, wire-bar coating, blade coating, roller coating, curtain coating, slit-die coating, gravure coating, slit reverse coating, micro gravure coating, comma coating, and the like.

The composition used in the present invention can be used singly. The composition used in the present invention may be optionally combined with natural or synthetic fibers, such as cellulose acetate, polyamide, polyester, polycarbonate, polysulfone, polyethersulfone, polyolefin, polytetrafluoroethylene derivatives, or paper; or with inorganic fibers, such as glass or alumina, within a range that does not impair the effect of the present invention. Examples of the form of the composition include pellets, films, sheets, plates, pipes, tubes, rods, granules, various special molded products, fibers, hollow filaments, woven fabrics, knitted fabrics, non-woven fabrics, and the like.

The method for producing pellets comprising the composition of the present invention is not limited, and any known pelletizing method can be used; however, a preferable method is tablet compression that can produce pellets with a higher density.

The method for producing sheets comprising the composition of the present invention is not limited, and any known sheet-forming method can be used; however, a preferable method is wet paper making that can produce sheets with a higher density. Wet paper making is a method in which raw materials are dispersed in water and filtered through a net, followed by drying.

An example of special molded products is a honeycomb shape. Any known processing method can be used to form sheets comprising the composition of the present invention into a honeycomb shape. "Honeycomb shape" as mentioned in the present invention refers to a shape of continuous hollow polygonal columns with a hexagonal cross section, as well as a square, sine-wave, or roll cross section; or a shape of continuous hollow cylindrical columns, such as cylinders. For example, sheets comprising the composition of the present invention are formed into a sine-wave honeycomb shape in the following manner. First, a sheet comprising the composition of the present invention is passed through shaping rolls to form a wave-shaped sheet, and a flat sheet is bonded to one or both sides of the wave-shaped sheet. These sheets are laminated to form a sine-wave honeycomb filter. Here, it is common to fix the sheets with an adhesive that is put on the top of the wave shapes. However, when wave-shaped sheets comprising the composition of the present invention are laminated, a flat sheet placed between the wave-shaped sheets is necessarily fixed; thus, an adhesive is not necessarily used. When an adhesive is used, it is necessary to use one that does not impair the adsorption performance of the sheets. Usable adhesives are, for example, corn starch, vinyl acetate resin, and acrylic resin. The gas adsorption performance of the wave-shaped sheet comprising the composition of the present invention can be enhanced by reducing the adhesion pitch of the sheet and lowering the thread height of the sheet. The pitch is preferably 0.5 to 8 mm, and the thread height is preferably 0.4 to 5 mm.

The composition used in the present invention may contain, if necessary, one or more members selected from antioxidants, anti-freezing agents, pH adjusters, masking agents, coloring agents, oils, flame retardants, near-infrared absorbers, ultraviolet absorbers, color tone correcting agents, dyes, and other specific functional agents, within a range that does not impair the effect of the present invention.

Owing to its excellent adsorption performance with respect to various gases, the adsorbent material of the present invention can be suitably used as an adsorbent material for adsorbing carbon dioxide, hydrogen, carbon monoxide, oxygen, nitrogen, hydrocarbons having 1 to 4 carbon atoms (such as methane, ethane, ethylene, acetylene, propane, propene, methylacetylene, propadiene, butane, 1-butene, isobutene, and butadiene), noble gases (such as helium, neon, argon, krypton, and xenon), hydrogen sulfide, ammonia, water vapor, and organic vapor. Accordingly, a gas adsorption method using the adsorbent material of the present invention is also within the technical scope of the invention. The term "organic vapor" means a vaporizing gas of an organic substance that is in liquid form at ordinary temperature under ordinary pressure. Examples of such an organic substance include alcohols, such as methanol and ethanol; amines, such as trimethylamine and pyridine; aldehydes, such as acetaldehyde; aliphatic hydrocarbons having 5 to 16 carbon atoms, such as pentane, isoprene, hexane, cyclohexane, heptane, methylcyclohexane, octane, 1-octene, cyclooctane, cyclooctene, 1,5-cyclooctadiene, 4-vinyl-1-cyclohexene, and 1,5,9-cyclododecatriene; aromatic hydrocarbons, such as benzene, toluene, and xylene; ketones, such as acetone and methyl ethyl ketone; esters, such as methyl acetate and ethyl acetate; and halogenated hydrocarbons, such as methyl chloride and chloroform.

The adsorption method comprises a step of bringing a gas and the adsorbent material of the present invention to be in contact with each other under the condition that enables the gas to be adsorbed to the metal complex in the adsorbent material. The condition, i.e., the adsorption pressure and the adsorption temperature that enable the gas to be adsorbed to the metal complex in the adsorbent material, can be suitably set according to the type of substance to be adsorbed. For example, the adsorption pressure is preferably 0.01 to 10 MPa, and more preferably 0.1 to 3.5 MPa. The adsorption temperature is preferably 195 to 343 K, and more preferably 273 to 313 K.

Moreover, owing to its excellent storage performance with respect to various gases, the adsorbent material of the present invention can be suitably used as a storage material for storing carbon dioxide, hydrogen, carbon monoxide, oxygen, nitrogen, hydrocarbons having 1 to 4 carbon atoms (such as methane, ethane, ethylene, acetylene, propane, propene, methylacetylene, propadiene, butane, 1-butene, isobutene, and butadiene), noble gases (such as helium, neon, argon, krypton, and xenon), hydrogen sulfide, ammonia, water vapor, and organic vapor. Accordingly, a gas storage method using the adsorbent material of the present invention is also within the technical scope of the invention. The term "organic vapor" means a vaporizing gas of an organic substance that is in liquid form at ordinary temperature under ordinary pressure. Examples of such an organic substance include alcohols, such as methanol and ethanol; amines, such as trimethylamine and pyridine; aldehydes, such as acetaldehyde; aliphatic hydrocarbons having 5 to 16 carbon atoms, such as pentane, isoprene, hexane, cyclohexane, heptane, methylcyclohexane, octane, 1-octene, cyclooctane, cyclooctene, 1,5-cyclooctadiene, 4-vinyl-1-cyclohexene, and 1,5,9-cyclododecatriene; aromatic hydrocarbons, such as benzene, toluene, and xylene; ketones, such as acetone and methyl ethyl ketone; esters, such as methyl acetate and ethyl acetate; and halogenated hydrocarbons, such as methyl chloride and chloroform.

The storage method comprises a step of bringing a gas and the storage material of the present invention to be in contact with each other under the condition that enables the gas to be adsorbed to the metal complex in the storage material. The condition, i.e., the adsorption pressure and the adsorption temperature that enable the gas to be adsorbed to the metal complex in the storage material, can be suitably set according to the type of substance to be adsorbed. For example, the adsorption pressure is preferably 0.01 to 10 MPa, and more preferably 0.1 to 3.5 MPa. The adsorption temperature is preferably 195 to 343 K, and more preferably 273 to 313 K.

The storage method further comprises a step of reducing the pressure from an adsorption pressure to a pressure enabling the gas to be desorbed from the metal complex in the storage material. The desorption pressure can be suitably set according to the type of substance to be adsorbed. For example, the desorption pressure is preferably 0.005 to 2 MPa, and more preferably 0.01 to 0.1 MPa. The storage method otherwise comprises a step of increasing the temperature from an adsorption temperature to a temperature enabling the gas to be desorbed from the metal complex in the storage material. The desorption temperature can be suitably set according to the type of substance to be adsorbed. For example, the desorption temperature is preferably 303 to 473 K, and more preferably 313 to 373 K.

Taking advantage of its storage performance, the adsorbent material of the present invention can be used in the production of gas storage devices. For example, the adsorbent material can be used in a gas storage device that comprises a pressure-resistant container that can be hermetically sealed and has an inlet and outlet for gas, wherein the pressure-resistant container has a gas storage space, and wherein a storage material comprising the adsorbent material of the present invention is placed in the gas storage space. A desired gas is stored in the gas storage device by compressing the gas into the gas storage device so that the gas is adsorbed by the storage material placed therein. The gas is taken out from the gas storage device by opening a pressure valve to reduce the internal pressure in the pressure-resistant container, thereby desorbing the gas. When the storage material is placed in the gas storage space, pellets obtained by molding the adsorbent material of the present invention may be used, in terms of handling properties, etc.

Figure 4:
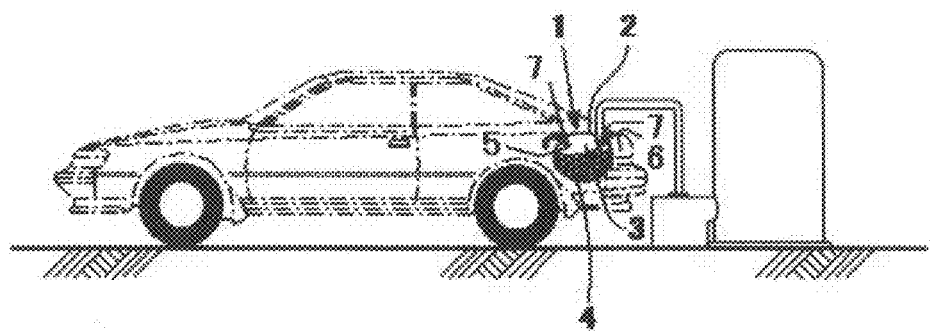
FIG. 4: A conceptual diagram illustrating a gaseous-fuel vehicle comprising a gas storage device.

FIG. 4 shows an example of a gaseous-fuel vehicle comprising the gas storage device of the present invention described above. The gas storage device can store fuel gas in a gas storage space 3, and can be suitably used as a fuel tank 1 of a gaseous-fuel vehicle, etc. The gaseous-fuel vehicle comprises, as a fuel tank 1, the above gas storage device in which the adsorbent material of the present invention is placed, and also comprises an engine as an internal combustion engine that receives natural gas stored in the fuel tank 1, and mixes the natural gas with oxygen-containing gas for combustion (e.g., air), thereby obtaining running driving force by combustion of the gas mixture. The fuel tank 1 comprises a pressure-resistant container 2, a pair of outlet 5 and inlet 6 for enabling a gas to be stored to enter or exit the container 2, and a pair of valves 7 each provided in the outlet and inlet and constituting a hermetically sealed mechanism that can maintain the gas in the container 2 in a pressurized state. The fuel tank 1 is filled with fuel (natural gas) in a pressurized state at a gas station. The fuel tank 1 is internally provided with a storage material 4 comprising the adsorbent material of the present invention. The storage material 4 adsorbs the natural gas (e.g., gas comprising methane as a main component) at ordinary temperature under increased pressure. When the valve 7 on the outlet side is opened, the adsorbed gas is desorbed from the storage material 4, and transmitted to the engine side such that the gas is combusted to generate running driving force.

The fuel tank 1, which is internally provided with the storage material of the present invention, has higher gas compressibility relative to the apparent pressure, compared to a fuel tank without the storage material. The thickness of the tank can be thereby reduced, and the weight of the entire gas storage device can also be reduced, which is advantageous for gaseous fuel vehicles, etc. In addition, the fuel tank 1 is generally maintained at ordinary temperature, without cooling. When the temperature increases (e.g., during summer), the temperature of the tank becomes relatively high. The storage material of the present invention is able to maintain its high storage ability in such a high temperature range (about 298 to 333 K), and is therefore useful.

Furthermore, owing to its excellent separation performance with respect to various gases, the adsorbent material of the present invention can be suitably used as a separation material for separating carbon dioxide, hydrogen, carbon monoxide, oxygen, nitrogen, hydrocarbons having 1 to 4 carbon atoms (such as methane, ethane, ethylene, acetylene, propane, propene, methylacetylene, propadiene, butane, 1-butene, isobutene, or butadiene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, and organic vapor. The separation material is particularly suitable for separating carbon dioxide from methane, carbon dioxide from hydrogen, carbon dioxide from nitrogen, ethane from methane, ethylene from ethane, or methane from the air, by using, for example, a pressure swing adsorption process or a temperature swing adsorption process. Accordingly, a method for separating the above gases using the adsorbent material of the present invention is also within the technical scope of the invention. The term "organic vapor" means a vaporizing gas of an organic substance that is in liquid form at ordinary temperature under ordinary pressure. Examples of such an organic substance include alcohols, such as methanol and ethanol; amines, such as trimethylamine and pyridine; aldehydes, such as acetaldehyde; aliphatic hydrocarbons having 5 to 16 carbon atoms, such as pentane, isoprene, hexane, cyclohexane, heptane, methylcyclohexane, octane, 1-octene, cyclooctane, cyclooctene, 1,5-cyclooctadiene, 4-vinyl-1-cyclohexene, and 1,5,9-cyclododecatriene; aromatic hydrocarbons, such as benzene, toluene, and xylene; ketones, such as acetone and methyl ethyl ketone; esters, such as methyl acetate and ethyl acetate; and halogenated hydrocarbons, such as methyl chloride and chloroform.

The separation method comprises a step of bringing a gas and the separation material of the present invention to be in contact with each other under the condition that enables the gas to be adsorbed to the separation material. The condition, i.e., the adsorption pressure and the adsorption temperature that enable the gas to be adsorbed to the separation material, can be suitably set according to the type of substance to be adsorbed. For example, the adsorption pressure is preferably 0.01 to 10 MPa, and more preferably 0.1 to 3.5 MPa. The adsorption temperature is preferably 195 to 343 K, and more preferably 273 to 313 K.

The pressure swing adsorption process or the temperature swing adsorption process may be used as the separation method. When performing the pressure swing adsorption process as the separation method, the separation method further comprises a step of increasing the pressure from an adsorption pressure to a pressure enabling the gas to be desorbed from the metal complex in the separation material. The desorption pressure can be suitably set according to the type of substance to be adsorbed. For example, the desorption pressure is preferably 0.005 to 2 MPa, and more preferably 0.01 to 0.1 MPa. When performing the temperature swing adsorption process as the separation method, the separation method further comprises a step of increasing the temperature from an adsorption temperature to a temperature enabling the gas to be desorbed from the metal complex. The desorption temperature can be suitably set according to the type of substance to be adsorbed. For example, the desorption temperature is preferably 303 to 473 K, and more preferably 313 to 373 K.

When performing the pressure swing adsorption process or the temperature swing adsorption process as the separation method, the step of bringing the gas to be in contact with the separation material and the step of changing the pressure or the temperature that enable the gas to be desorbed from the separation material may be appropriately repeated.

EXAMPLES

The invention will hereinafter be described specifically by using Examples and Comparative Examples. It should be borne in mind, however, that the invention is not limited to or limited by these examples. The analysis and evaluation in the following Examples and Comparative Examples were conducted as described below.

(1) Single-Crystal X-Ray Crystal Structure Analysis

The resulting single crystal was mounted on a gonio head and subjected to measurement using a single-crystal X-ray diffractometer. Details of the measurement conditions are shown below. The volume change rate was determined from the results of the structure analysis by comparing the volume of the structural unit of the metal complex (A) before and after adsorption/desorption of a synthetic solvent.

Measurement Conditions

Apparatus: SMART APEX II Ultra (trade name; product of Bruker AXS K.K.)

X-Ray Source: MoKα ($\lambda$=0.71073 Å) 50 kV 24 mA

Collection Mirror: Helios

Detector: CCD

Collimator: 0.42-mm diameter

Analysis Software: SHELXTL (2) Measurement of Adsorption and Desorption Isotherms The amount of gas adsorbed was measured by the volumetric method (according to JIS Z8831-2) using a gas adsorption measuring instrument to create adsorption and desorption isotherms. Before measurement, the sample was dried at 373 K and 0.5 Pa for 5 hours to remove adsorbed water and the like. The following are details of the measurement conditions.

Measurement Conditions

Apparatus: BELSORP-HP (trade name; product of Bel Japan, Inc.)

Equilibrium Waiting Time: 500 sec.

In the measurement results of adsorption and desorption isotherms, the horizontal axis represents an equilibrium pressure expressed by MPa, and the vertical axis represents an equilibrium adsorption amount expressed by mL (STP)/g. In the measurement results of adsorption and desorption isotherms, the adsorption amounts (ads.) of the gases (such as carbon dioxide, methane, ethylene, ethane, and nitrogen) under increased pressure and the adsorption amounts (des.) of the gases under decreased pressure are plotted for each pressure level. STP (standard temperature and pressure) denotes a state at a temperature of 273.15 K and a pressure of 1 bar ($10^5$ Pa).

Synthesis Example 1

Figure 5:
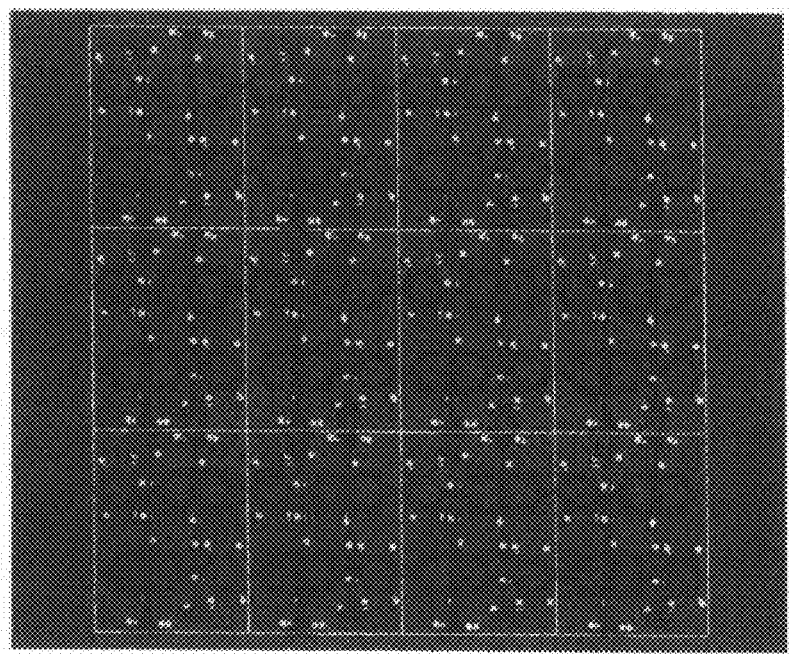
FIG. 5: A crystal structure of a metal complex obtained in Synthesis Example 1 before vacuum drying.

Under nitrogen atmosphere, 28.1 g (95 mmol) of zinc nitrate hexahydrate, 15.7 g (95 mmol) of terephthalic acid, and 7.39 g (47 mmol) of 4,4'-bipyridyl were dissolved in 8,000 mL of a mixed solvent containing N,N-dimethylformamide and ethanol at a capacity ratio of 1:1. The mixture was stirred at 363 K for 48 hours. The precipitated metal complex was subjected to single-crystal X-ray structure analysis. The result is shown below. The crystal structure is shown in FIG. 5. FIG. 5 reveals that the complex has a three-dimensional structure in which two jungle-gym-type frameworks are interpenetrated into each other.

Triclinic (P-1)
a=10.880(3)Å
b=10.918(3)Å
c=14.122(4)Å
α=89.335(16)°
β=89.171(17)°
γ=78.380(16)°
V=1643.0(8)Å$^3$
Z=2
R=0.0655
wR=0.1697

After collecting the precipitated metal complex by suction filtration, the metal complex was washed three times with methanol. Subsequently, the metal complex was dried for 8 hours at 373 K, 50 Pa, thereby obtaining 27.5 g of the target metal complex (yield=95%). The obtained metal complex was subjected to single-crystal X-ray structure analysis. The result is shown below. The crystal structure is shown in FIG. 6.

Triclinic (P-1)
a=7.7911(13)Å
b=9.2984(18)Å
c=10.6284(19)Å
α=65.320(7)°
β=86.199(7)°
γ=78.145(7)°
V=684.6(2)Å$^3$
Z=2
R=0.0325
wR=0.0836

Figure 6:
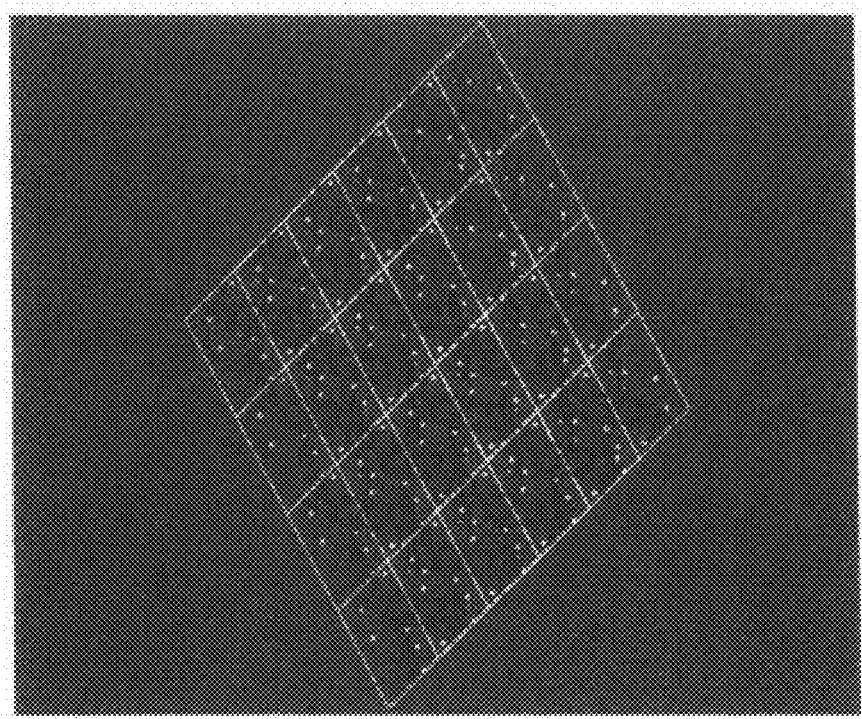
FIG. 6: A crystal structure of a metal complex obtained in Synthesis Example 1 after vacuum drying.

Comparison between FIG. 5 and FIG. 6 reveals that the structure changes before and after the adsorption and desorption of the synthetic solvent. This shows that the structure of this complex dynamically changes due to the adsorption and desorption. The volume change rate in this case is 20.0%, which is calculated by using the volume of the structural unit of the metal complex before vacuum drying (=1643.0(8)Å$^3$) and the volume of the structural unit of the metal complex after vacuum drying (=684.6(2)Å$^3$), and according to the following formula:

$$\text{Volume change rate} = [1 - 1643.0/(684.6 \times 2)] \times 100 = 20.0\%$$

Synthesis Example 2

Figure 7:
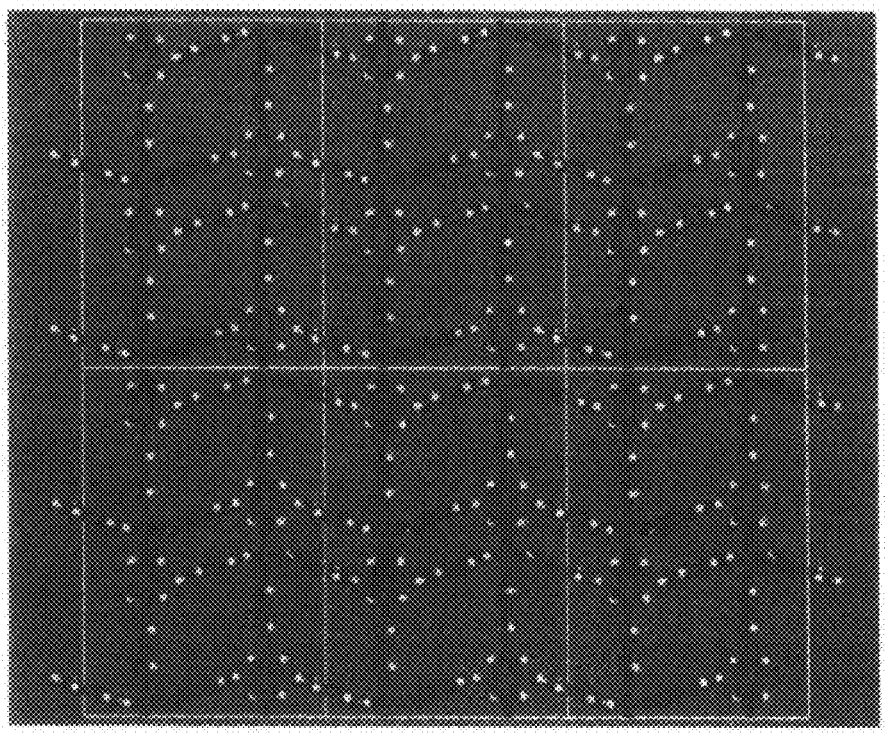
FIG. 7: A crystal structure of a metal complex obtained in Synthesis Example 2 before vacuum drying.

A solution of 4,4'-bipyridyl in acetone with a concentration of 0.08 mol/L (2,000 mL) and a solution of 2,5-dihydroxybenzoic acid in acetone with a concentration of 0.32 mol/L (2,000 mL) were added dropwise to 1,000 mL of an aqueous solution of copper acetate (0.04 mol/L) over 2 hours. The mixture was then stirred at 298 K for 2 hours. The precipitated metal complex was subjected to single-crystal X-ray structure analysis. The result is shown below. The crystal structure is shown in FIG. 7. FIG. 7 reveals that the complex has a three-dimensional structure in which two-dimensional-sheet-type frameworks are interpenetrated into each other.

Monoclinic (C2/c)
a=16.270(2)Å
b=22.132(3)Å
c=15.473(2)Å
α=90.00°
β=99.435(2)°
γ=90.00°
V=5496.1(14)Å³
Z=8
R=0.0563
wR=0.1622

After collecting the precipitated metal complex by suction filtration, the metal complex was washed three times with acetone. Subsequently, the metal complex was dried for 8 hours at 373 K, 50 Pa, thereby obtaining 36.6 g of the target metal complex (yield=87%). The obtained metal complex was subjected to single-crystal X-ray structure analysis. The result is shown below. The crystal structure is shown in FIG. 8.

Triclinic (P-1)
a=6.633(3)Å
b=8.092(4)Å
c=11.001(5)Å
α=85.256(6)°
β=76.058(6)°
γ=78.326(5)°
V=560.9(4)Å³
Z=1
R=0.0520
wR=0.1309

Figure 8:
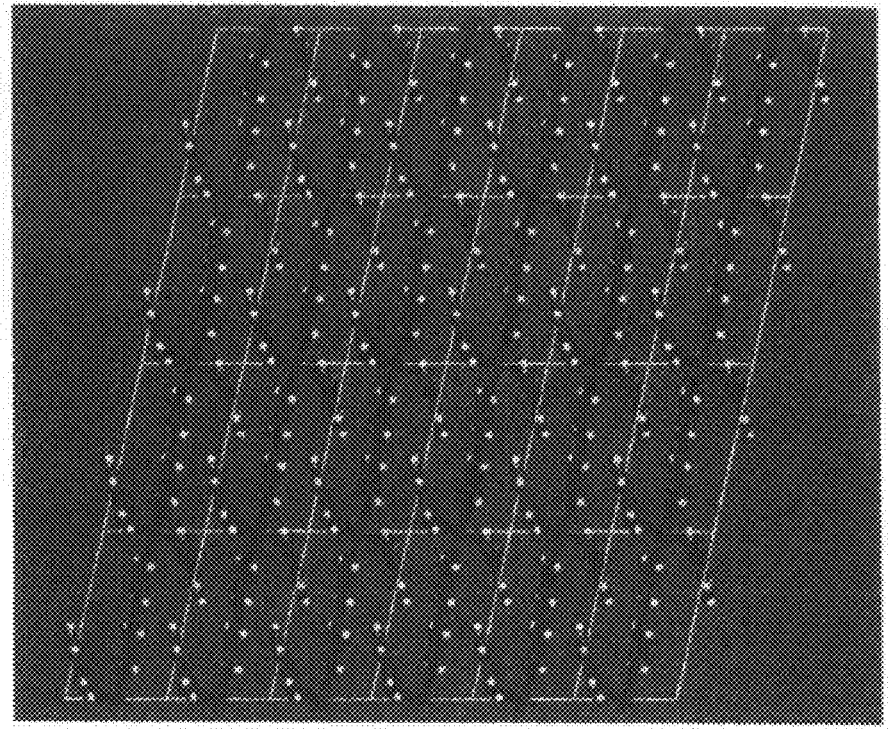
FIG. 8: A crystal structure of a metal complex obtained in Synthesis Example 2 after vacuum drying.

Comparison between FIG. 7 and FIG. 8 reveals that the structure changes before and after the adsorption and desorption of the synthetic solvent. This shows that the structure of this complex dynamically changes due to the adsorption and desorption. The volume change rate in this case is 22.5%, which is calculated by using the volume of the structural unit of the metal complex before vacuum drying (=5496.1(14)Å³) and the volume of the structural unit of the metal complex after vacuum drying (=560.9(4)Å³), and according to the following formula:

$$\text{Volume change rate}=[1-5496.1/(560.9\times 8)]\times 100=22.5\%$$

Example 1

An olefin elastomer (Milastomer® 5030NS, produced by Mitsui Chemicals, Inc.; 0.50 g) was swollen in toluene, and then kneaded with 2.0 g of the metal complex obtained in Synthesis Example 1 in a mortar, thereby obtaining a composition. The composition was placed in a cylindrical mold (inner diameter: 3.0 mm; length: 15 mm), and molded into a pellet shape having a diameter of 3.0 mm and a length of 15 mm. The obtained pellet composition was dried for 8 hours at 373 K, 50 Pa, thereby obtaining 2.4 g of the target composition (yield=95%).

Figure 9:
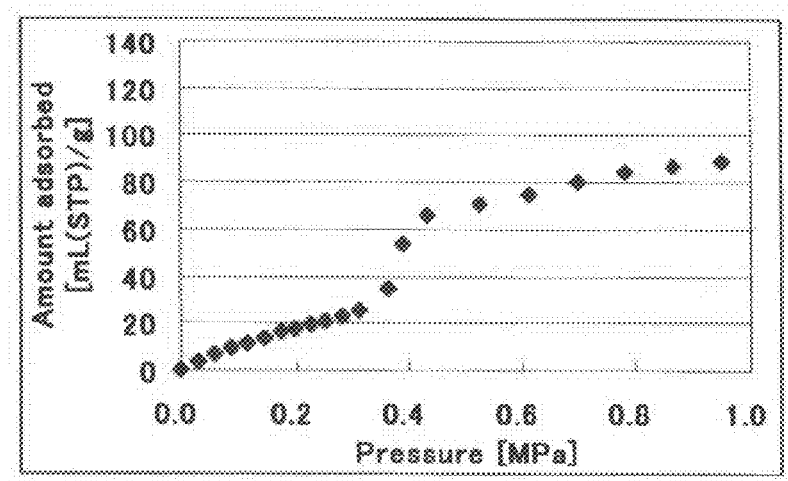
FIG. 9: An adsorption isotherm of carbon dioxide on a composition obtained in Example 1 at 273 K.

The amount of carbon dioxide adsorbed by the obtained pellet composition at 273 K was measured according to the volumetric method to plot an adsorption isotherm. The adsorption isotherm is shown in FIG. 9. In this case, there was no significant difference in pellet size before and after gas adsorption.

Comparative Example 1

The metal complex (0.96 g) obtained in Synthesis Example 1 and 0.24 g of a polytetrafluoroethylene homopolymer (Teflon® 6-J, produced by Dupont-Mitsui Fluorochemicals Co., Ltd.) were kneaded in a mortar, thereby obtaining a composition. The composition was placed in a mill (inner diameter: 3.0 mm; length: 15 mm), and subjected to tablet compression at 200 kgf using a simple tablet press (HANDTAB-100, produced by Ichihashi Seiki Co., Ltd.) to mold the composition into a pellet shape having a diameter of 3.0 mm and a length of 15 mm.

Figure 10:
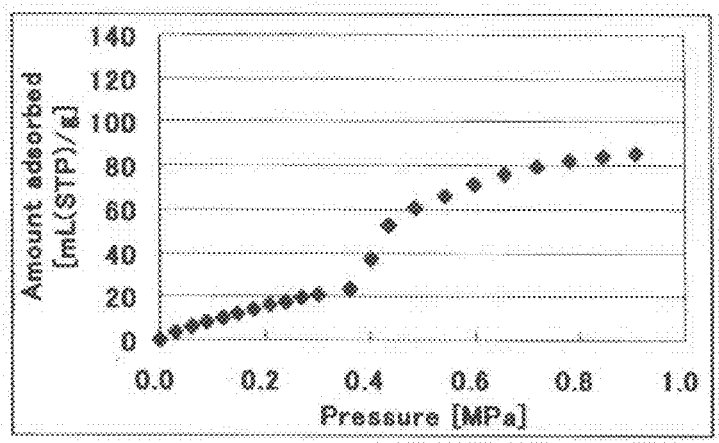
FIG. 10: An adsorption isotherm of carbon dioxide on a composition obtained in Comparative Example 1 at 273 K.

The amount of carbon dioxide adsorbed by the obtained pellet composition at 273 K was measured according to the volumetric method to plot an adsorption isotherm. The adsorption isotherm is shown in FIG. 10. In this case, the pellet size after gas adsorption was expanded from the pellet size before gas adsorption by 6.7% in the diameter direction (changed to 3.2 mm) and 20% in the length direction (changed to 18 mm).

Reference Example 1

Figure 11:
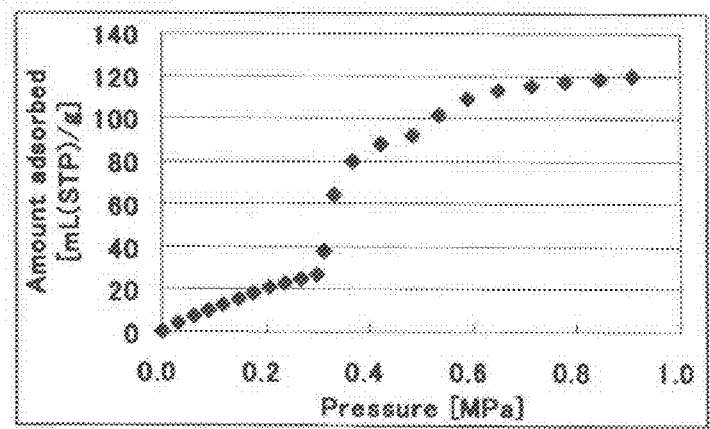
FIG. 11: An adsorption isotherm of carbon dioxide on a metal complex obtained in Synthesis Example 1 at 273 K.

The amount of carbon dioxide adsorbed by the unmolded metal complex obtained in Synthesis Example 1 at 273 K was measured according to the volumetric method to plot an adsorption isotherm. The adsorption isotherm is shown in FIG. 11.

Comparison between Example 1 and Comparative Example 1 reveals that the adsorbent material comprising the composition of Example 1, which satisfies the constituent features of the present invention, is excellent as an adsorbent material for carbon dioxide, because it adsorbs carbon dioxide along with the increase in pressure and does not undergo irreversible expansion before and after adsorption of carbon dioxide. In addition, comparison between Example 1 and Reference Example 1 reveals that the adsorbent material comprising the composition of the present invention maintains the original adsorption performance of the metal complex after molding, because the adsorption starting pressure does not become higher than the starting pressure of the metal complex in a powder form before molding.

Example 2

An acrylic elastomer (a methyl methacrylate-butyl acrylate block copolymer: Kurarity™, produced by Kuraray Co., Ltd.; 2.0 g) was added to 30 mL of toluene, and dissolved by stirring at 298 K. The metal complex obtained in Synthesis Example 1 (8.0 g) was added to the resulting solution, and the mixture was stirred at 298 K for 2 hours. The toluene was then removed under reduced pressure to form a paste. The paste was placed in a cylindrical mold (inner diameter: 3.0 mm; length: 15 mm), and molded into a pellet shape having a diameter of 3.0 mm and a length of 15 mm. The obtained pellet composition was dried for 8 hours at 373 K, 50 Pa, thereby obtaining 9.3 g of the target composition (yield=93%).

Figure 12:
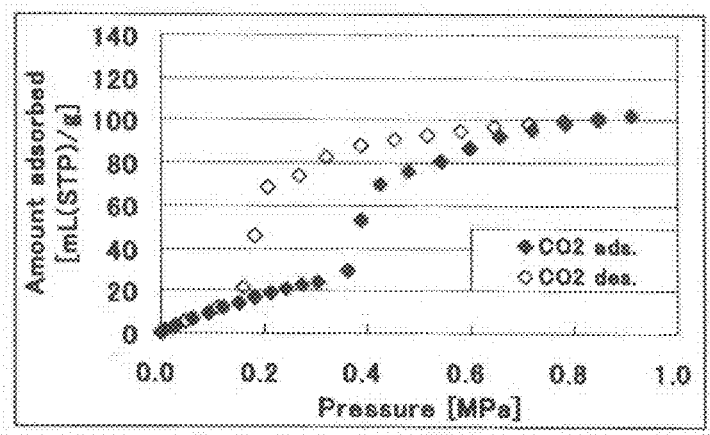
FIG. 12: Adsorption and desorption isotherms of carbon dioxide on a composition obtained in Example 2 at 273 K.

The amounts of carbon dioxide adsorbed and desorbed by the obtained pellet composition at 273 K were measured according to the volumetric method to plot adsorption and desorption isotherms. The adsorption and desorption isotherms are shown in FIG. 12, and the result is shown in Table 1. In this case, there was no significant difference in pellet size before and after gas adsorption.

Example 3

A pellet composition was obtained in the same manner as in Example 2, except that a styrene elastomer (a hydrogenated styrene-isoprene block copolymer: Septon™, produced by Kuraray Co., Ltd.) was used in place of acrylic elastomer (Kurarity™, produced by Kuraray Co., Ltd.).

Figure 13:
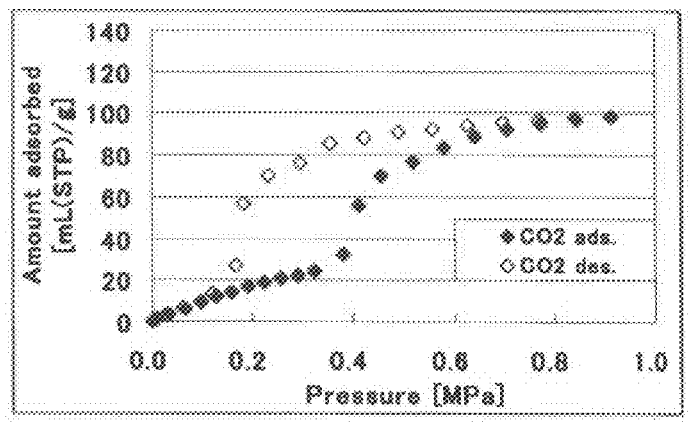
FIG. 13: Adsorption and desorption isotherms of carbon dioxide on a composition obtained in Example 3 at 273 K.

The amounts of carbon dioxide adsorbed and desorbed by the obtained composition at 273 K were measured according to the volumetric method to plot adsorption and desorption isotherms. The adsorption and desorption isotherms are shown in FIG. 13, and the result is shown in Table 1. In this case, there was no significant difference in pellet size before and after gas adsorption.

Example 4

An amide elastomer (Pebax® 2533SA01, produced by Arkema; 0.50 g) was added to 20 mL of toluene, and dissolved by stirring at 383 K. After cooling the mixture to 298 K, 2.0 g of the metal complex obtained in Synthesis Example 1 was added to the resulting solution, and stirred at 298 K for 2 hours. The toluene was then removed under reduced pressure to form a paste. The paste was placed in a cylindrical mold (inner diameter: 3.0 mm; length: 15 mm), and molded into a pellet shape having a diameter of 3.0 mm and a length of 15 mm. The obtained pellet composition was dried for 8 hours at 373 K, 50 Pa, thereby obtaining 2.3 g of the target composition (yield=92%).

Figure 14:
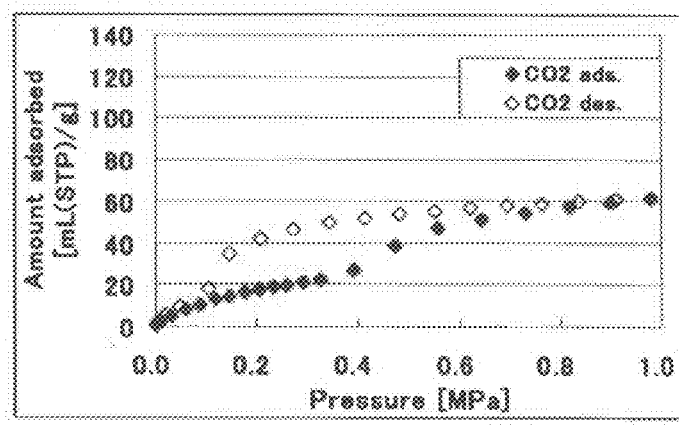
FIG. 14: Adsorption and desorption isotherms of carbon dioxide on a composition obtained in Example 4 at 273 K.

The amounts of carbon dioxide adsorbed and desorbed by the obtained pellet composition at 273 K were measured according to the volumetric method to plot adsorption and desorption isotherms. In this case, there was no significant difference in pellet size before and after gas adsorption. The adsorption and desorption isotherm are shown in FIG. 14, and the result is shown in Table 1.

Example 5

Figure 15:
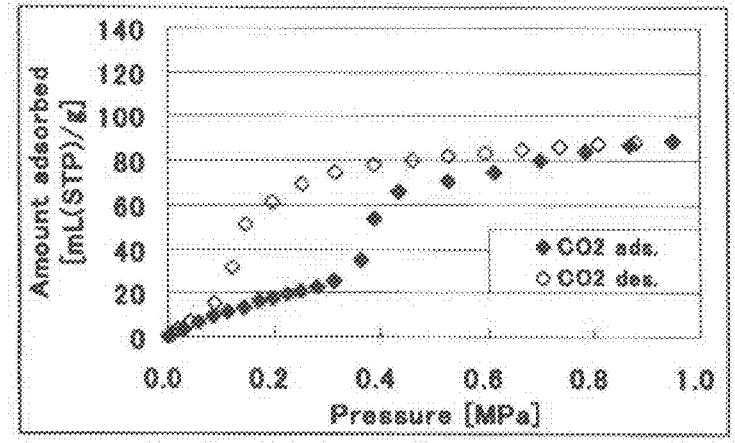
FIG. 15: Adsorption and desorption isotherms of carbon dioxide on a composition obtained in Example 5 at 273 K.

A pellet composition comprising the metal complex of Synthesis Example 1 and an olefin elastomer was prepared in the same manner as in Example 1. The amounts of carbon dioxide adsorbed and desorbed by the obtained pellet composition at 273 K were measured according to the volumetric method to plot adsorption and desorption isotherms. The adsorption and desorption isotherms are shown in FIG. 15, and the result is shown in Table 1. In this case, there was no significant difference in pellet size before and after gas adsorption.

Example 6

Using a Laboplastomill (produced by Toyo Seiki Seisakusho, Ltd.), 39 g of an acrylic elastomer (a methyl methacrylate-butyl acrylate block copolymer; Kurarity™, produced by Kuraray Co., Ltd.) and 39 g of the metal complex obtained in Synthesis Example 2 were melted and kneaded at a rotation speed of 100 rpm at 313 K for 10 minutes, thereby obtaining a composition. Subsequently, the composition was kneaded at 313 K by using a MiniMax molder (produced by Custom Scientific Instruments Inc.), and then extruded into a strand shape having a diameter of 3.0 mm. The obtained strand was cut into a length of 15 mm, thereby obtaining a pellet composition.

Figure 16:
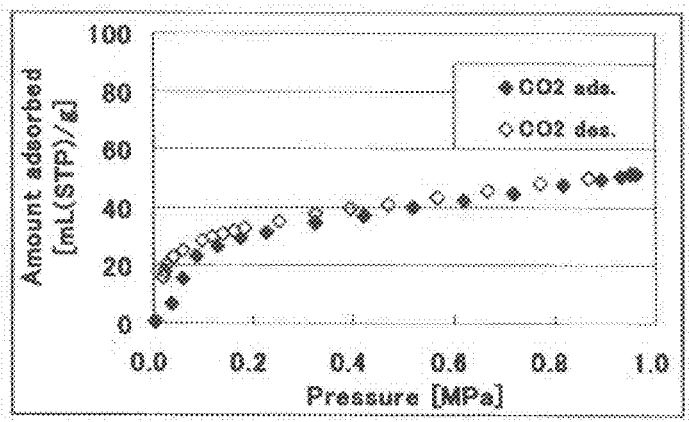
FIG. 16: Adsorption and desorption isotherms of carbon dioxide on a composition obtained in Example 6 at 273 K.

Adsorption and desorption isotherms of carbon dioxide on the obtained pellet composition at 273 K were measured. The adsorption and desorption isotherms are shown in FIG. 16, and the result is shown in Table 1. In this case, there was no significant difference in pellet size before and after gas adsorption.

Comparative Example 2

Figure 17:
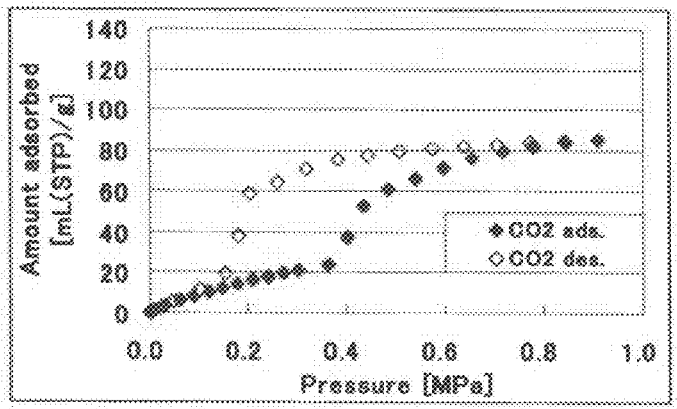
FIG. 17: Adsorption and desorption isotherms of carbon dioxide on a composition obtained in Comparative Example 2 at 273 K.

A pellet composition comprising the metal complex of Synthesis Example 1 and a polytetrafluoroethylene homopolymer was prepared in the same manner as in Comparative Example 1. The amounts of carbon dioxide adsorbed and desorbed by the obtained pellet composition at 273 K were measured according to the volumetric method to plot adsorption and desorption isotherms. The adsorption and desorption isotherms are shown in FIG. 17, and the result is shown in Table 1. In this case, the pellet size after gas adsorption was expanded from the pellet size before gas adsorption by 6.7% in the diameter direction (changed to 3.2 mm) and 20% in the length direction (changed to 18 mm).

Reference Example 2

Figure 18:
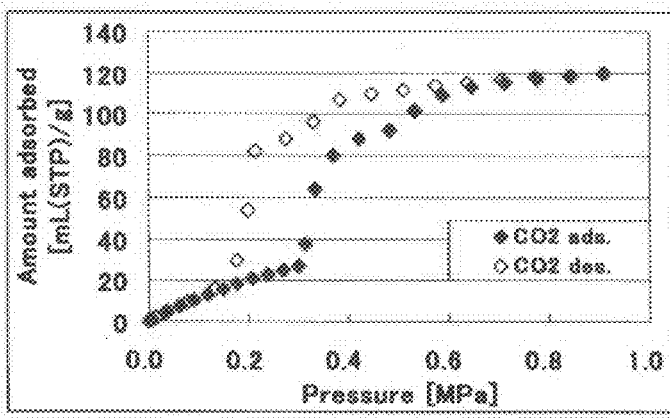
FIG. 18: Adsorption and desorption isotherms of carbon dioxide on a metal complex obtained in Synthesis Example 1 at 273 K.

The amounts of carbon dioxide adsorbed and desorbed by the unmolded metal complex obtained in Synthesis Example 1 at 273 K were measured according to the volumetric method to plot adsorption and desorption isotherms. The adsorption and desorption isotherms are shown in FIG. 18, and the result is shown in Table 1.

Reference Example 3

Figure 19:
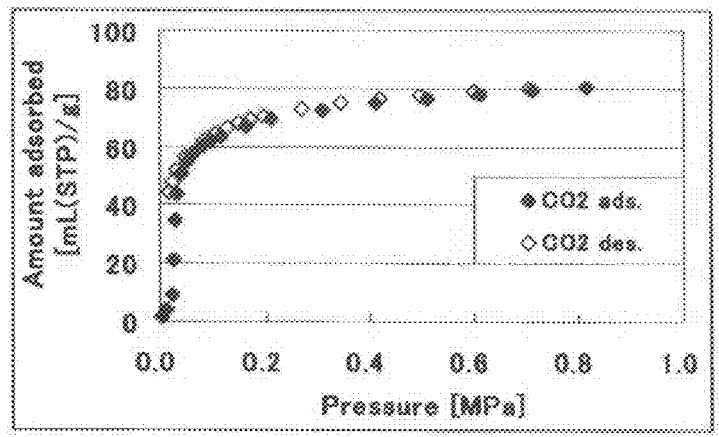
FIG. 19: Adsorption and desorption isotherms of carbon dioxide on a metal complex obtained in Synthesis Example 2 at 273 K.

The amounts of carbon dioxide adsorbed and desorbed by the unmolded metal complex obtained in Synthesis Example 2 at 273 K were measured according to the volumetric method to plot adsorption and desorption isotherms. The adsorption and desorption isotherms are shown in FIG. 19, and the result is shown in Table 1.

TABLE 1

| | Adsorbent material | | | | Adsorption | Equilibrium adsorption | |
| | Metal complex (A) | Elastomer (B) | A:B | Adsorption/ desorption isotherms | starting pressure (MPa) | amount at 0.9 MPa (mL (STP)/g) | Pellet expansion |
| --- | --- | --- | --- | --- | --- | --- | --- |
| Ex. 2 | Synth. Ex. 1 | Acrylic elastomer | 80:20 | FIG. 12 | 0.38 | 100 (125*) | No |
| Ex. 3 | Synth. Ex. 1 | Styrene elastomer | 80:20 | FIG. 13 | 0.40 | 100 (125*) | No |
| Ex. 4 | Synth. Ex. 1 | Amide elastomer | 80:20 | FIG. 14 | 0.40 | 60 (75*) | No |
| Ex. 5 | Synth. Ex. 1 | Olefin elastomer | 80:20 | FIG. 15 | 0.39 | 82 (103*) | No |
| Ex. 6 | Synth. Ex. 2 | Acrylic elastomer | 50:50 | FIG. 16 | 0.05 | 50 (100*) | No |

TABLE 1-continued

| | Adsorbent material | | | Adsorption/desorption isotherms | Adsorption starting pressure (MPa) | Equilibrium adsorption amount at 0.9 MPa (mL (STP)/g) | Pellet expansion |
|---|---|---|---|---|---|---|---|
| | Metal complex (A) | Elastomer (B) | A:B | | | | |
| Comp. Ex. 2 | Synth. Ex. 1 | Polytetrafluoroethylene homopolymer | 80:20 | FIG. 17 | 0.39 | 80 (100*) | Yes |
| Ref. Ex. 2 | Synth. Ex. 1 | — | — | FIG. 18 | 0.32 | 120 | — |
| Ref. Ex. 3 | Synth. Ex. 2 | — | — | FIG. 19 | 0.01 | 80 | — |

*Equilibrium adsorption amount per metal complex

The equilibrium adsorption amount per metal complex in Table 1 was determined by the following formula using the proportion of the metal complex in the composition calculated from the A:B ratio.

Equilibrium adsorption amount per metal complex=equilibrium adsorption amount of entire composition/proportion of metal complex in composition Table 1 and FIGS. 12 to 16 reveal that the adsorbent materials comprising any of the compositions obtained in Examples 2 to 6 are excellent as storage materials, because they adsorbed a larger amount of carbon dioxide per metal complex, released the adsorbed carbon dioxide along with the decrease in pressure, without reducing the pressure to 0.1 MPa or less, and did not undergo irreversible expansion before and after adsorption and desorption of carbon dioxide.

In contrast, it is revealed that the adsorbent material comprising the composition of Comparative Example 2, which did not comprise the elastomer (B), is not suitable as a storage material, because expansion of the pellet was observed before and after adsorption and desorption of carbon dioxide. Furthermore, comparison between Examples 2 to 5 and Reference Example 2, and comparison between Example 6 and Reference Example 3 reveal that the adsorbent material comprising the composition of the present invention maintained the original storage performance of the metal complex after molding, because the adsorption starting pressure did not become higher than the starting pressure of the metal complex in a powder form before molding, and because the adsorption amount per metal complex contained in the composition was almost equal to that of the unmolded metal complex.

Example 7

Figure 20:
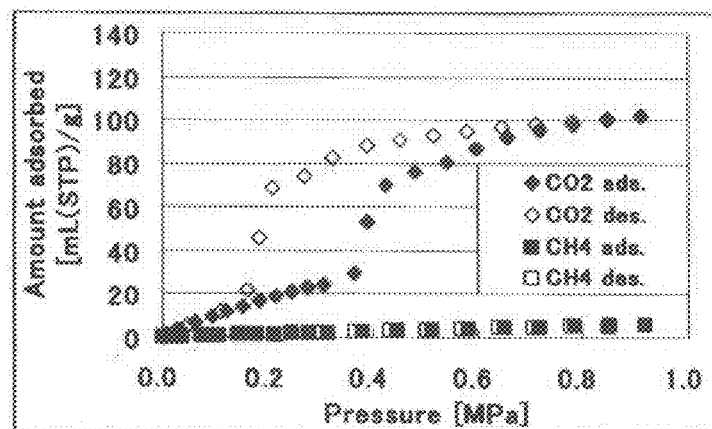
FIG. 20: Adsorption and desorption isotherms of carbon dioxide and methane on a composition obtained in Example 7 at 273 K.

A pellet composition comprising the metal complex of Synthesis Example 1 and an acrylic elastomer was prepared in the same manner as in Example 2. The amounts of carbon dioxide and methane adsorbed and desorbed by the pellet composition at 273 K were measured according to the volumetric method to plot adsorption and desorption isotherms. The adsorption and desorption isotherms are shown in FIG. 20. In this case, there was no significant difference in pellet size before and after gas adsorption.

Example 8

Figure 21:
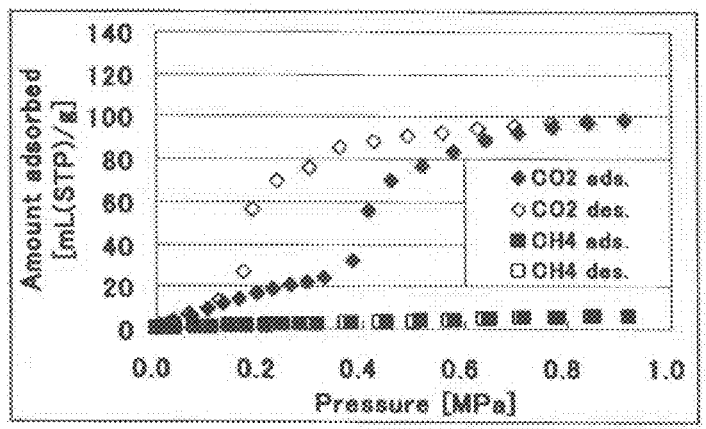
FIG. 21: Adsorption and desorption isotherms of carbon dioxide and methane on a composition obtained in Example 8 at 273 K.

A pellet composition comprising the metal complex of Synthesis Example 1 and a styrene elastomer was prepared in the same manner as in Example 3. The amounts of carbon dioxide and methane adsorbed and desorbed by the pellet composition at 273 K were measured according to the volumetric method to plot adsorption and desorption isotherms. The adsorption and desorption isotherms are shown in FIG. 21. In this case, there was no significant difference in pellet size before and after gas adsorption.

Comparative Example 3

Figure 22:
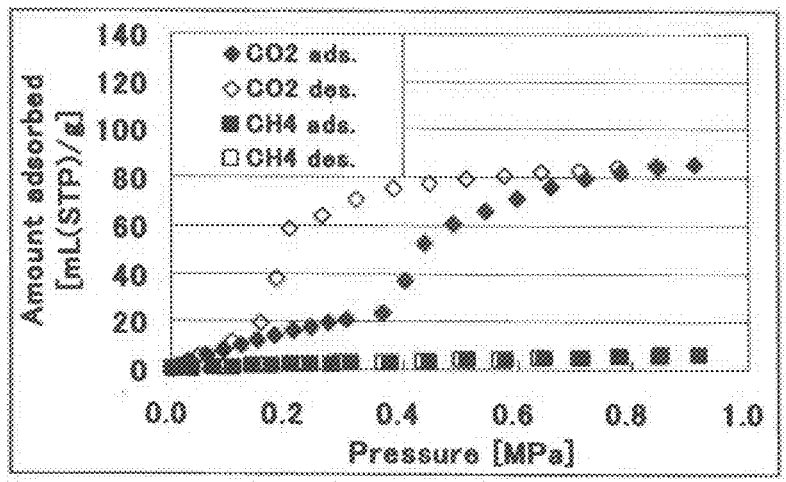
FIG. 22: Adsorption and desorption isotherms of carbon dioxide and methane on a composition obtained in Comparative Example 3 at 273 K.

A pellet composition comprising the metal complex of Synthesis Example 1 and a polytetrafluoroethylene homopolymer was prepared in the same manner as in Comparative Example 1. The amounts of carbon dioxide and methane adsorbed and desorbed by the pellet composition at 273 K were measured according to the volumetric method to plot adsorption and desorption isotherms. The adsorption and desorption isotherms are shown in FIG. 22. In this case, the pellet size after gas adsorption increased from the pellet size before gas adsorption by 6.7% in the diameter direction (changed to 3.2 mm) and 20% in the length direction (changed to 18 mm).

Reference Example 4

Figure 23:
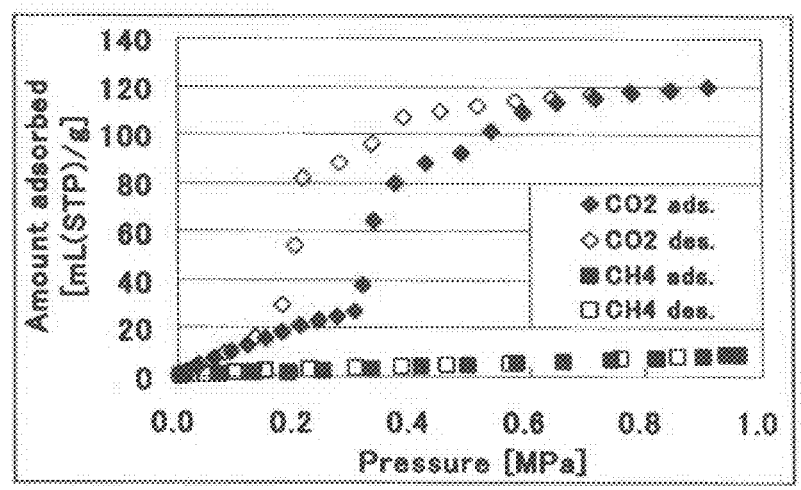
FIG. 23: Adsorption and desorption isotherms of carbon dioxide and methane on a metal complex obtained in Synthesis Example 1 at 273 K.

The amounts of carbon dioxide and methane adsorbed and desorbed by the unmolded metal complex obtained in Synthesis Example 1 at 273 K were measured according to the volumetric method to plot adsorption and desorption isotherms. The adsorption and desorption isotherms are shown in FIG. 23.

Comparison between Examples 7 and 8, and Comparative Example 3 reveals that the adsorbent material of the present invention is excellent as a separation material, because the adsorbent materials comprising either of the compositions of Examples 7 and 8, which satisfy the constituent features of the present invention, selectively adsorb carbon dioxide along with the increase in pressure, release the carbon dioxide along with the decrease in pressure, and do not undergo irreversible expansion during adsorption and desorption of carbon dioxide. In addition, comparison with Reference Example 4 also reveals that the adsorbent materials comprising either of the compositions of Examples 7 and 8 have separation performance almost equal to that of the metal complex before molding.

The above results clearly show that combining a metal complex with an elastomer is an excellent method of shaping a metal complex, because combining a metal complex with an elastomer does not impair the original adsorption performance, storage performance, or separation performance of the metal complex, and because the shape can be maintained even after gas adsorption. Although the reason for such effects is unclear, it is considered that due to the use of an elastic elastomer, the expansion of the composition is adsorbed without suppressing the volume change of the metal complex.

The adsorbent material comprising the composition of the present invention has excellent gas adsorption performance, gas storage performance, and gas separation performance, maintains its shape without volume expansion upon adsorption of gas after molding, and exhibits gas adsorption/desorption performance equal to that of the composition before molding. The adsorbent material is thus useful as an adsorbent material, a storage material, or a separation material, for various gases. The use of the adsorbent material of the present invention can provide a gas separation device that has less increase in ventilation resistance and less pressure loss.

REFERENCE NUMERAL LIST

1. Fuel tank as a gas storage device
2. Pressure-resistant container
3. Gas storage space
4. Storage material
5. Outlet
6. Inlet
7. Valve

The invention claimed is:

1. An adsorbent material, comprising a composition comprising:
   a metal complex (A); and
   an elastomer (B),
   wherein:
   the metal complex (A) comprises an anionic ligand and at least one metal ion of a Group 1 to 13 metal of the periodic table;
   the metal complex (A) undergoes a volume change upon adsorption; and
   a mass ratio of the metal complex (A) to the elastomer (B) is within a range of 1:99 to 99:1.

2. The adsorbent material according to claim 1, wherein the metal complex (A) futher comprises an organic ligand that undergoes multidentate binding to the metal ion.

3. The adsorbent material according to claim 1, wherein a volume change rate of the metal complex (A) upon adsorption is 0.5 to 50%.

4. The adsorbent material according to claim 1, wherein the elastomer (B) is a thermoplastic elastomer comprising at least one polymer block having a glass transition temperature of 273 K or less.

5. The adsorbent material according to claim 1, which absorbs carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.

6. A storage material comprising the adsorbent material of claim 1.

7. The storage material according to claim 6, which is adapted to storing carbon dioxide, hydrogen, carbon monoxide, oxygen, nitrogen, hydrocarbons having 1 to 4 carbon atoms, noble gases, hydrogen sulfide, ammonia, water vapor, or organic vapor.

8. A gas storage device, comprising
   a pressure-resistant container that can be hermetically sealed and comprising an inlet and outlet for gas, and a gas storage space therein; and
   the storage material of claim 6 located within the gas storage space.

9. A gaseous-fuel vehicle, comprising an internal combustion engine that is configured to obtain driving force from a fuel gas supplied from the gas storage device of claim 8.

10. A separation material, comprising the adsorbent material of claim 1.

11. The separation material according to claim 10, which separates carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.

12. A separation method, comprising contacting the separation material of claim 10 with a gas mixture at a pressure ranging from 0.01 to 10 MPa.

13. The separation method according to claim 12, wherein separation of components in the gas mixture occurs by a pressure swing adsorption process or a temperature swing adsorption process.

14. The adsorbent material according to claim 2, wherein a volume change rate of the metal complex (A) upon adsorption is 0.5 to 50%.

15. The adsorbent material according to claim 2, wherein the elastomer (B) is a thermoplastic elastomer comprising at least one polymer block having a glass transition temperature of 273 K or less.

* * * * *